United States Patent [19]
Kubota et al.

[11] Patent Number: 5,606,411
[45] Date of Patent: Feb. 25, 1997

[54] INSPECTING METHOD FOR DISK USED IN PHOTO FILM CASSETTE

[75] Inventors: Masayuki Kubota; Yuzo Tsunekawa, both of Minami-Ashigara, Japan

[73] Assignee: Fuji Photo Film Co., Ltd., Kanagawa, Japan

[21] Appl. No.: 657,592

[22] Filed: Jun. 7, 1996

[30] Foreign Application Priority Data

Jun. 9, 1995 [JP] Japan .................................. 7-143438

[51] Int. Cl.⁶ .................................................. G01N 21/00
[52] U.S. Cl. ........................... 356/237; 356/394; 356/373; 356/392
[58] Field of Search ...................... 356/237, 373, 356/375, 153, 392, 394, 397

[56] References Cited

U.S. PATENT DOCUMENTS

| | | | |
|---|---|---|---|
| 4,423,943 | 1/1984 | Gold | 354/275 |
| 4,834,306 | 5/1989 | Robertson et al. | 242/71.1 |
| 4,848,693 | 7/1989 | Robertson | 242/71.1 |
| 5,271,577 | 12/1993 | Takahashi et al. | 242/71.16 |
| 5,407,146 | 4/1995 | Takahashi et al. | 242/348 |

Primary Examiner—Frank Gonzalez
Assistant Examiner—Reginald A. Ratliff
Attorney, Agent, or Firm—Sughrue, Mion, Zinn, Macpeak & Seas

[57] ABSTRACT

A photo film cassette has a spool core (13) about which the photo film is wound in a roll form. A flexible disk (16, 17) is secured to each of two ends of the spool core, for regulating each of edges of the photo film. Material of the disk being thermoplastic synthetic resin sheet (27). The sheet is subjected to vacuum/air-pressure forming to form a disk-like portion (50). The disk is cut out of the disk-like portion by a punch/die set (31) before conveyance to a spool core mounting station. To inspect the disk, a photoelectric switch (54) includes a projector (54a) for applying a beam to a die of the punch/die set after cutting out the disk. A receiver (54b) measures the beam reflected by the die. A controller (55) evaluates the measured beam, to inspect occurrence of deposition of the disk on the punch/die set. If the deposition occurs, the controller considers the disk likely to overlie on one subsequent disk.

43 Claims, 16 Drawing Sheets

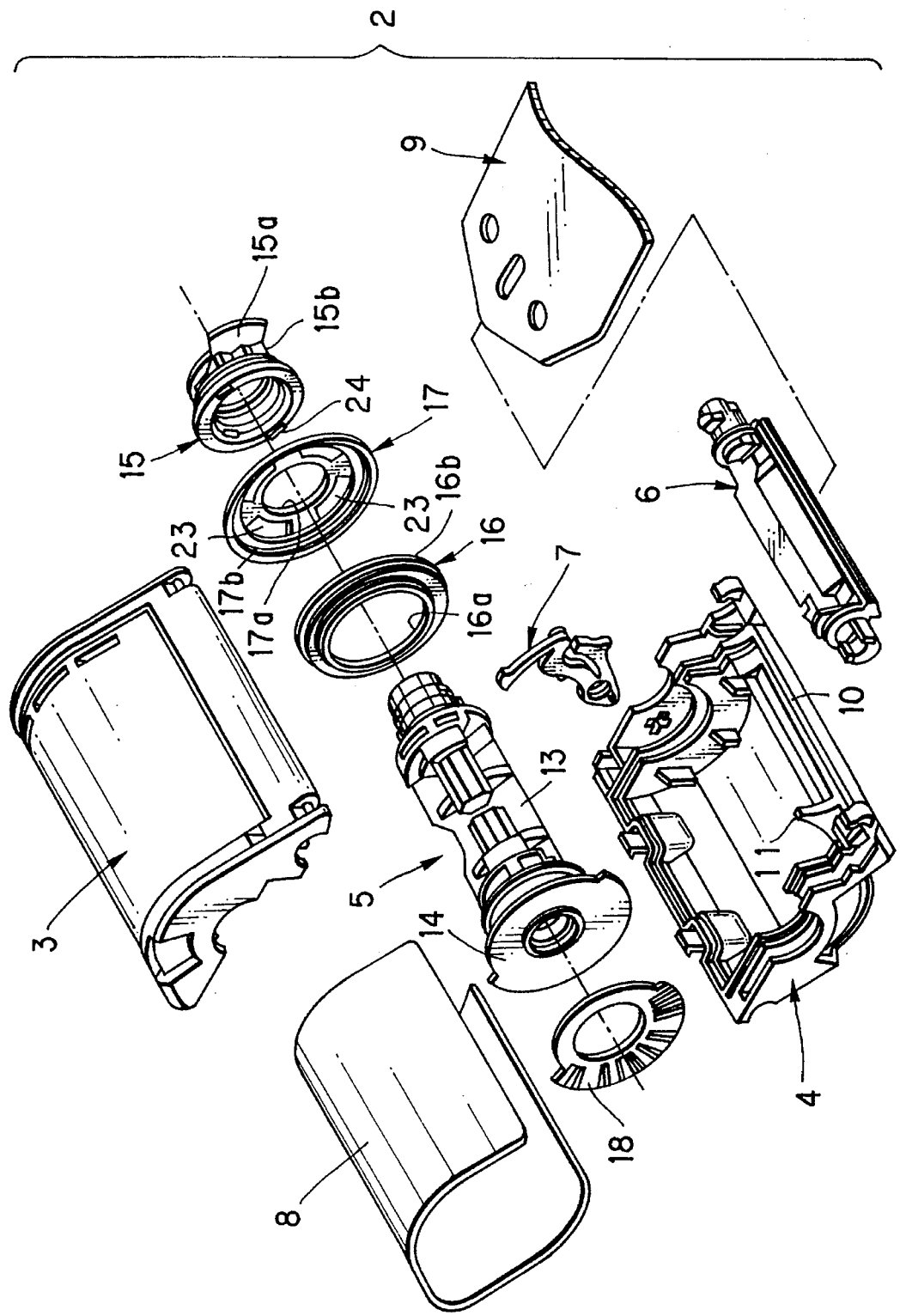

F I G. 2C
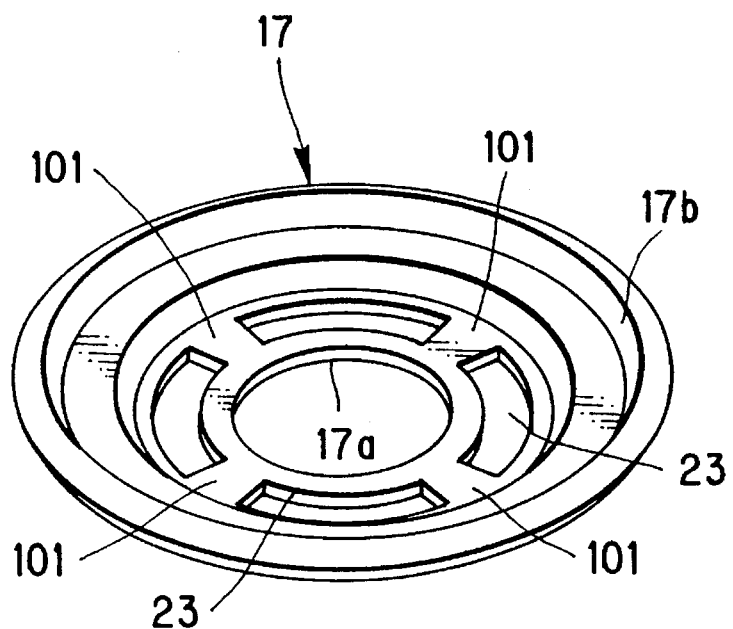
F I G. 2D
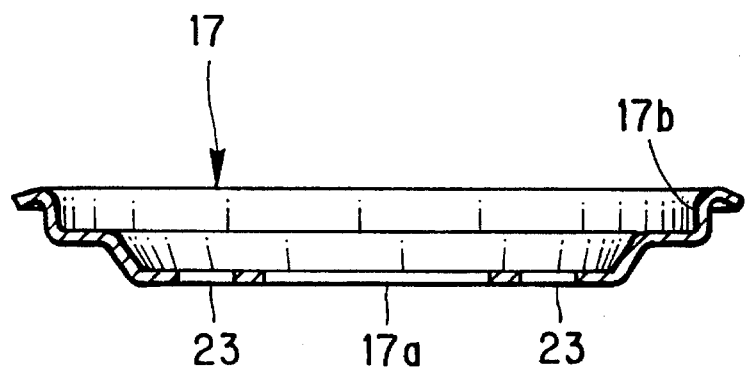

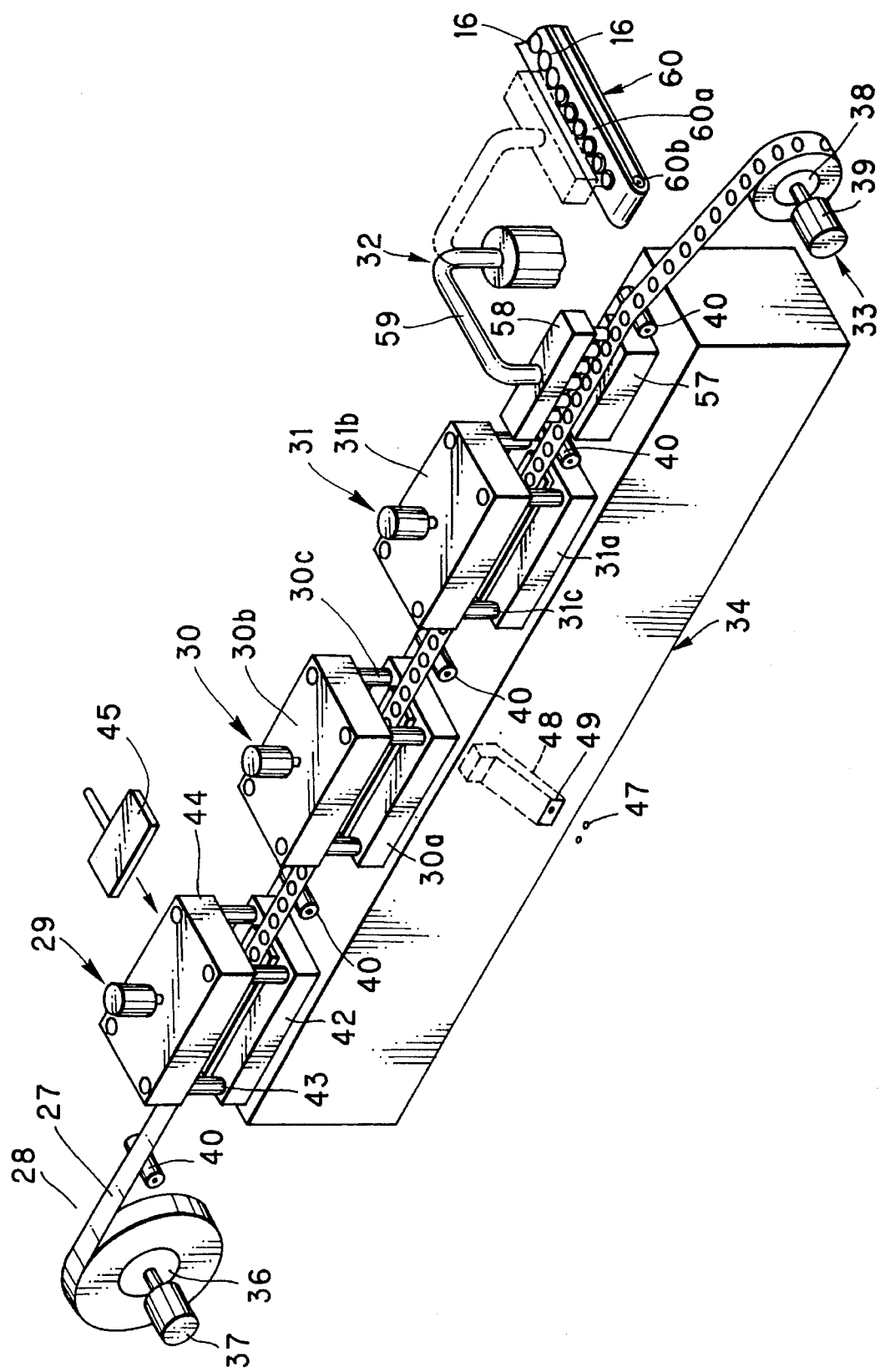

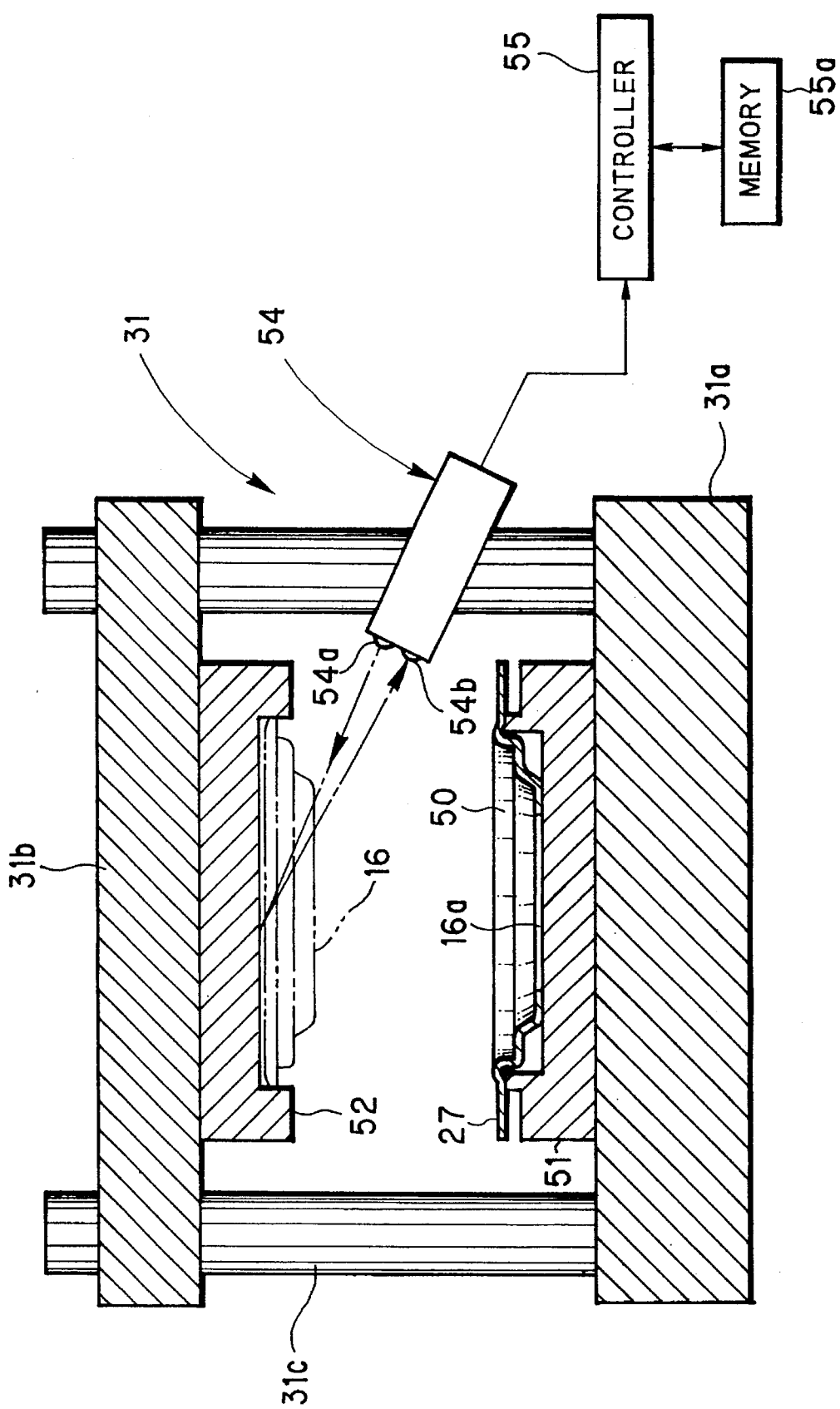

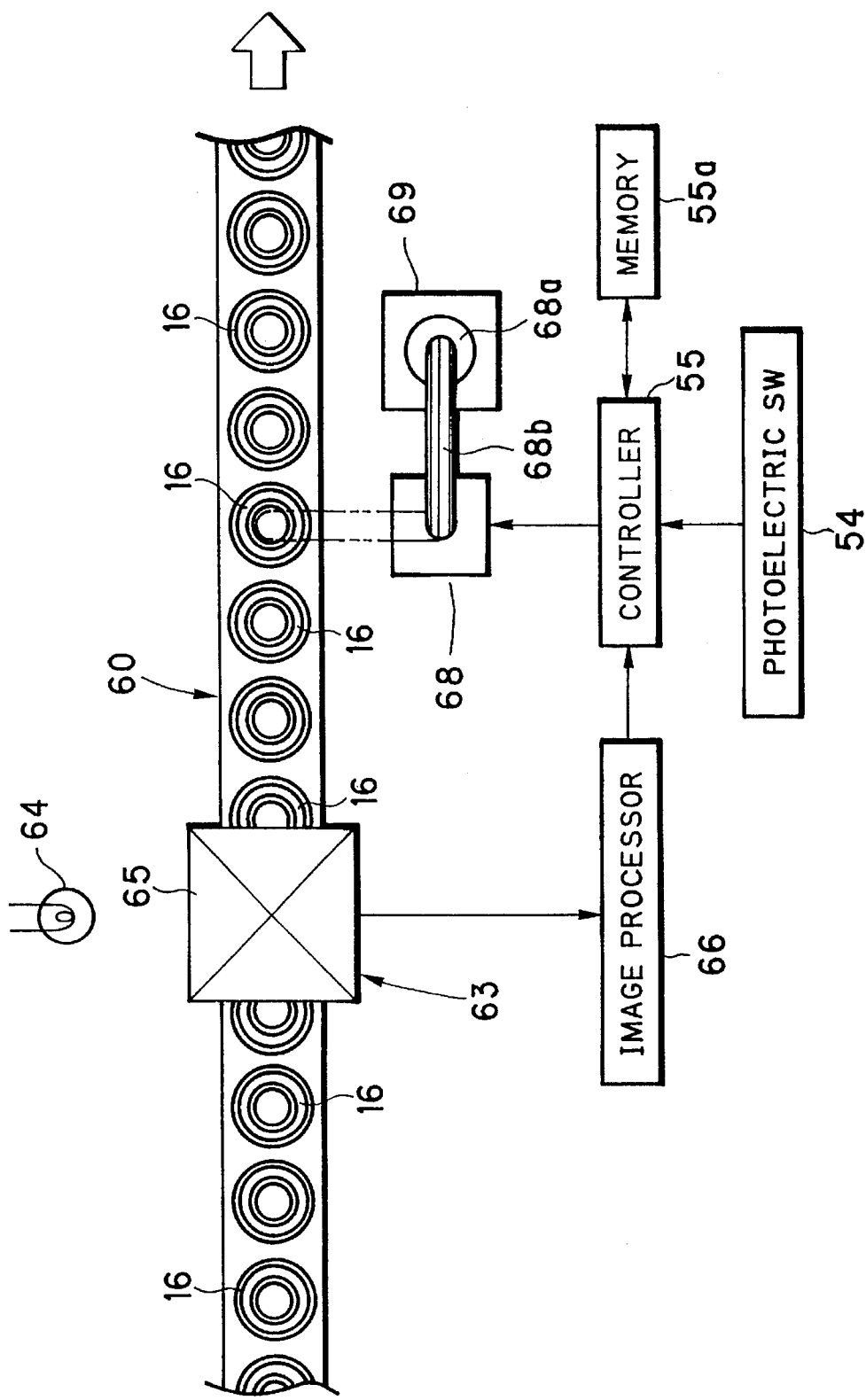

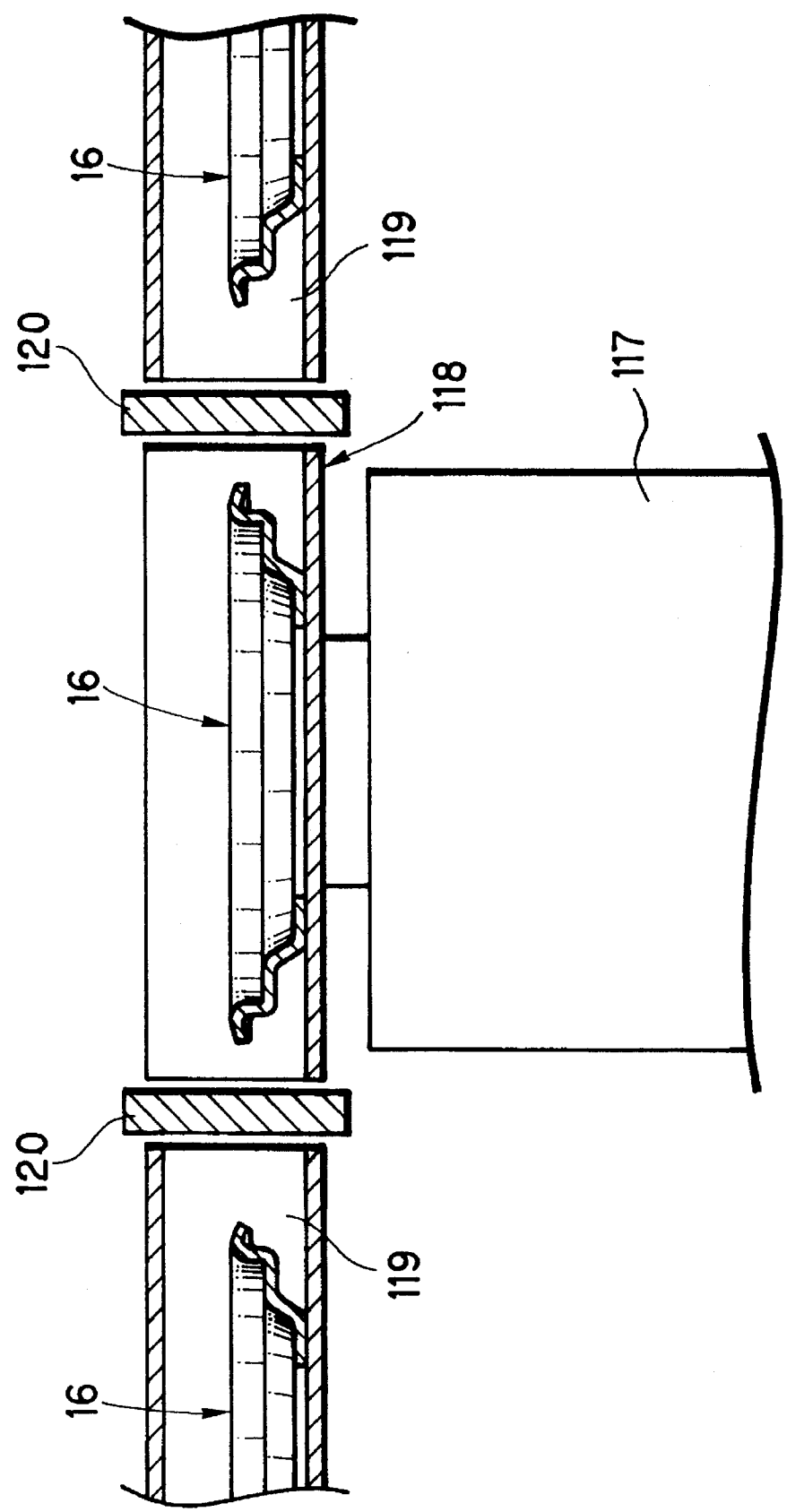

INSPECTING METHOD FOR DISK USED IN PHOTO FILM CASSETTE

BACKGROUND OF THE INVENTION

1. Field of the Invention

The present invention relates to an inspecting method for a flexible disk for use in a photo film cassette. More particularly, the present invention relates to a flexible disk inspecting method in which an unacceptable disk in a line of producing a photo film cassette can be discovered with great efficiency.

2. Description Related to the Prior Art

U.S. Pat. No. 4,423,943 discloses a type of photo film cassette, of which a leader of unexposed photo film is precontained in the cassette shell, and advanced to an outside of the cassette shell when a spool is rotated in an unwinding direction. The spool is constituted by a spool core and two flexible disks, which are disposed on the spool core, for contact with the ends of a roll of the photo film, to render the turns of the photo film neat. In the cassette of the leader-advancing type, it is necessary to transmit rotation of the spool to the roll of the photo film. To this end, the disks of the spool are provided with respective ring-like lips formed on their periphery and projected toward one another. The ring-like lips are located to cover edges of the outermost turn of the photo film, and prevent the roll from being loosened. Such a cassette is suggested in U.S. Pat. Nos. 4,834,306, 4,848,693 (corresponding to JP-A 2-18545), U.S. Pat. No. 5,271,577 (corresponding to JP-A 3-37645), and U.S. Pat. No. 5,407,146 (corresponding to JP-A 3-37645).

To advance the leader of the photo film, it is necessary to spread both flexible disks in the vicinity of a photo film passageway, to release the ring-like lips from regulation. The disks are rotatable, and are not rotated without being deformed. The disks are formed at a sufficiently small thickness. To form disks, various methods are known: vacuum forming, air-pressure forming, vacuum/air-pressure forming in combination of those, injection molding, and the like.

In the flexible disk producing method, continuous resin sheet of a thermoplastic type having small thickness is heated. The continuous sheet is deformed for example in accordance with the vacuum/air-pressure forming. The continuous sheet is moved into punch/die sets, where a punch device and a die device cut a bearing hole and then a circular contour at each disk-like portion, to form the disks. The disks as cut out of the continuous sheet are conveyed to a line for combination with spool cores.

In punching the flexible disk out of the continuous sheet, there is possibility of occurrence of burr on the disk or sticking of deposits such as dust created by the punching. If the disk has the burr or deposits, the disk, when contained in the cassette shell, cannot be properly rotated therein. The photo film would fail to be advanced. Or else the photo film would be scratched or damaged.

There is a possibility of depositing the flexible disk on the inside of a die blade of the punch/die set upon punching the disk-like portion in the continuous sheet. If the punching operation is continued, the disk remaining deposited is overlaid on another later disk. The two overlaid disks will be accidentally mounted on the spool core and contained in the cassette shell. One of the overlaid disks would come to have a reduced inner diameter of the two-stepped dish shape, so that the photo film would not be wrapped by the disk properly. The disk would be degraded in the flexibility, and could not be deformed by the photo film, which could not be advanced.

SUMMARY OF THE INVENTION

In view of the foregoing problems, an object of the present invention is to provide an inspecting method for a flexible disk for use in a photo film cassette, capable of discovering an unacceptable disk in a line of producing a photo film cassette with great efficiency.

In order to achieve the above and other objects and advantages of this invention, a flexible disk inspecting method comprises a first inspecting process of inspecting a shape of a disk, to detect the disk acceptable or unacceptable, and/or a second inspecting process of inspecting occurrence of overlay of the disk on another disk before a spool core mounting station, to detect the disk unacceptable if the overlay occurs.

In a preferred embodiment, a measuring device is disposed upstream from the spool core mounting station, for measuring a shape of the disk to obtain disk information. A memory previously stores reference information. A detector device compares the disk information with the reference information read from the memory, so as to detect the disk unacceptable if the disk information is different from the reference information.

In addition, a photoelectric switch of a reflection type includes a projector for applying an electromagnetic ray to a blade of the punch/die set after cutting out the disk. A receiver measures the electromagnetic ray reflected by the blade. A controller evaluates the measured electromagnetic ray, to inspect occurrence of deposition of the disk on the punch/die set, and if the deposition occurs, the controller considering the disk likely to overlie on one subsequent disk.

In another preferred embodiment, a photoelectric switch of a transmission or reflection type includes a projector for applying an electromagnetic ray to the sheet in a station downstream from the punch/die set relative to conveyance of the sheet. A receiver measures the electromagnetic ray from the sheet. A controller evaluates the measured electromagnetic ray, to check existence of the disk in the punch hole, and if the disk does not exist, the controller considering the disk likely to overlie on one subsequent disk cuttable by the punch/die set.

Further, a pressure switch measures sucking pressure of the sucker during the air suction. A controller evaluates the measured sucking pressure, and if the sucking pressure is zero, the controller detecting the disk not existing in the punch hole, and considering the disk likely to overlie on one subsequent disk cuttable by the punch/die set.

In still another preferred embodiment, the disk being translucent. A photoelectric switch of a transmission type includes a projector for applying an electromagnetic ray to the disk conveyed serially. A receiver detects the electromagnetic ray transmitted through the disk. A controller compares transmitted intensity of the electromagnetic ray with a predetermined threshold value, and if the transmitted intensity is lower than the threshold value, the controller detecting the disk overlaid on another disk.

In an additinal preferred embodiment, a measuring device measures thickness of the disk. A controller compares the thickness with a predetermined limit value, and if the thickness is greater than the limit value, the disk being detected unacceptable due to the overlay.

Otherwise, a measuring device measures weight of the disk. A controller compares the weight with a predetermined limit value, and if the weight is greater than the limit value, the disk being detected unacceptable due to the overlay.

Further, a movable conveyor plate is disposed over the disk conveyed serially toward the spool core mounting station. A disk sucker sucks the disk of the conveyor plate at a sucking force short of two times as much as weight of the disk, the conveyor plate being moved during sucking operation, to allow dropping the disk unacceptably overlaid on another disk without further conveyance.

In the present invention, it is possible to discover an unacceptable disk in a line of producing a photo film cassette with great efficiency.

BRIEF DESCRIPTION OF THE DRAWINGS

The above objects and advantages of the present invention will become more apparent from the following detailed description when read in connection with the accompanying drawings, in which:

FIG. 1 is an exploded perspective illustrating a photo film cassette;

FIGS. 2C and 2D are a perspective and a cross section respectively illustrating another flexible disk;

FIG. 3 is a perspective illustrating a disk producing apparatus;

FIG. 4 is a cross section illustrating a contour punch/die set with a controller;

FIG. 5 is an explanatory view illustrating a shape inspector;

FIG. 14 is an explanatory view illustrating a further preferred process of disk overlay inspection in which disk weight is checked.

DETAILED DESCRIPTION OF THE PREFERRED EMBODIMENT(S) OF THE PRESENT INVENTION

Figure 2A:
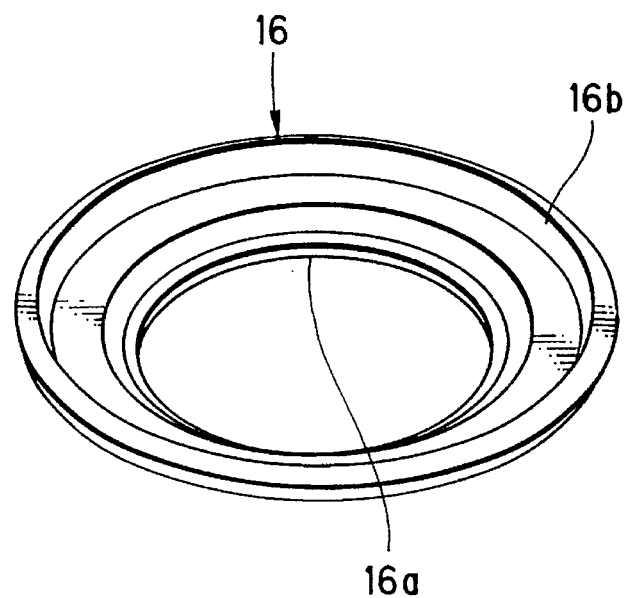
FIG. 2A is a perspective illustrating one flexible disk for use in the cassette.
Figure 2B:
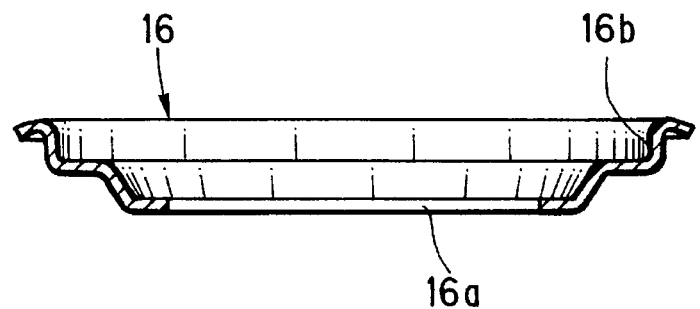
FIG. 2B is a cross section illustrating the disk.

In FIG. 1, a photo film cassette 2 includes upper and lower shell halves 3 and 4, a spool 5, a photo film port shutter 6, a lock lever 7 and a label or sticker 8. The shell halves 3 and 4 are respectively formed from plastics. The spool 5 is contained between the shell halves 3 and 4. The sticker 8 is attached to the outside of the shell halves 3 and 4. There is a photo film passage port 10 which is formed along a juncture between the shell halves 3 and 4 and through which photo film 9 is passed. Inside the photo film port 10, the port shutter 6 is mounted in rotatable fashion for opening/closing the photo film port 10. There is a separator claw 11, formed inward from the photo film port 10, for separating the leader of the photo film 9 about the spool 5 to direct it to the photo film port 10.

The spool 5 includes a spool core 13, a data plate 14, a barrel member 15, and flexible disks 16 and 17. There is a trailer of the photo film 9 secured to the spool core 13. The data plate 14 is formed on an axial end of the spool core 13. The barrel member 15 is secured to another axial end of the spool core 13. The disks 16 and 17 are secured to the spool core 13 between the data plate 14 and the barrel member 15. There is a bar code sticker 18 which is attached to the data plate 14 and has a bar code printed for representing various data of the photo film 9. The bar code is read by a reader of a camera or other external apparatuses.

The barrel member 15 includes an indicator plate 15a and a gear 15b. The indicator plate 15a indicates a used status of the photo film 9 to a user. The gear 15b is adapted to locking the spool 5. The indicator plate 15a is positioned at the inside of any of plural indicator windows formed in an end face of the shell halves 3 and 4, to signal information of any one of Unexposed, Partially Exposed, Exposed and Developed statuses, which are respectively associated with the indicator windows. The lock lever 7 is engaged with the gear 15b when the port shutter 6 has a closed position, to inhibit the spool 5 from rotating. When the port shutter 6 has an open position, the lock lever 7 is moved away from the gear 15b, to unlock the spool 5.

In FIGS. 2A–2D, the disks 16 and 17 respectively have a two-stepped dish shape, and have axial holes 16a and 17a into which the spool core 13 is inserted. Also the disks 16 and 17 have ring-like lips 16b and 17b projected from the periphery thereof to cover the outermost turn of the photo film 9 about the spool core 13. The disks 16 and 17 are formed from plastics at a small thickness facilitating deformation during advancement of the photo film 9.

As illustrated in FIGS. 2C and 2D, four arc-like slits 23 are formed in the disk 17 about the axial hole 17a. One face of the barrel member 15 has ratchet claws 24, which are inserted in the arc-like slits 23. When the spool 5 is rotated in the unwinding direction, the arc-like slits 23 are engaged with the ratchet claws 24, to rotate the disk 17 together with the spool core 13 When the spool 5 is rotated in the winding direction to wind the photo film, the ratchet claws 24 are moved past the arc-like slits 23, so that the disk 17 is free from rotation of the spool core 13.

The transmission of rotation to the disk 17 is changed over according to the rotational direction of the spool 5. The photo film 9 about the spool 5 and the disk 17 are rotated in integral fashion during the leader advancement, to reduce frictional resistance. This is effective to reduce force required for externally driving the spool 5 in advancing the photo film 9. Also the disk 17 is separately rotated in the operation to rewind the photo film. The photo film 9 can be wound inside the ring-like lip 17b without being hindered.

The photo film 9 of the photo film cassette 2 is contained fully in the photo film cassette 2 before and after the photo film 9 is used. The port shutter 6 is rotated to a position of closing the photo film port 10. Ambient light is kept from entering the photo film cassette 2 through the photo film port 10. The spool 5 is locked by the virtue of the lock lever 7, and hindered from rotating accidentally. When the port shutter 6 is opened in the photo film port 10 and the spool 5 is rotated in the clockwise direction, the photo film 9 is separated by the separator claw 11 and advanced through the photo film port 10.

FIG. 3 illustrates an apparatus 26 for producing the disk 16. The disk producing apparatus 26 is set up on a stand 34, and includes a sheet supply unit 28, a vacuum/air-pressure forming unit 29, a hole punch/die set 30, a contour punch/die set 31, a disk remover unit 32 and a sheet winder unit 33. The sheet supply unit 28 supplies the forming unit 29 with a continuous sheet 27 of thermoplastic synthetic resin as material of the disk 16. The forming unit 29 applies heat to the continuous sheet 27 and effects vacuum/air-pressure forming of five (5) disk-like portions on the continuous sheet 27 at one time. The hole punch/die set 30 cuts the axial hole 16a in each of the disk-like portions. The contour punch/die set 31 cuts the contour of the disk 16 to cut out the disk 16. The disk remover unit 32 removes the disk 16 from the disk producing apparatus 26. The continuous sheet winder unit 33 draws the continuous sheet 27 from the sheet supply unit 28, and winds the continuous sheet 27 after cutting the disk 16.

The continuous sheet 27 is 0.15 mm thick, and formed of resin of polystyrene-modified polyphenylene ether with elastomer added thereto. The ratio of polystyrene and polyphenylene ether is 3:7. The proportion of elastomer is 12 wt. %.

The sheet supply unit 28 includes a drum 36 and a brake 37. The drum 36 has the continuous sheet 27 wound thereabout. The brake 37 applies load to the drum 36, for applying tension to the continuous sheet 27 drawn by the sheet winder unit 33. The sheet winder unit 33 consists of a drum 38 and a motor 39. The drum 38 winds the continuous sheet 27 after the punching. The motor 39 rotates the drum 38. Guide rollers 40 are disposed between the sheet supply unit 28, the forming unit 29, the hole punch/die set 30, the contour punch/die set 31, the disk remover unit 32 and the sheet winder unit 33, for guiding the continuous sheet 27.

The forming unit 29 includes a stationary support 42 and a movable support 44. The stationary support 42 is fixed on the stand 34. The movable support 44 is guided by guide shafts 43 and movable up and down. The stationary support 42 has a female mold. The movable support 44 has a male mold. Those cooperate for forming the disk-like portions. Beside the forming unit 29, a sheet heater 45 is disposed, is inserted between the stationary support 42 and the movable support 44, and heats the continuous sheet 27.

When the continuous sheet 27 is conveyed to a position between the stationary support 42 and the movable support 44, the sheet heater 45 is inserted between them, to heat and soften the continuous sheet 27. When the continuous sheet 27 finishes being heated, the sheet heater 45 is retracted from between the stationary support 42 and the movable support 44. The movable support 44 is moved down toward the stationary support 42 by a hydraulic cylinder, a cam or the like. The air pressurization is effected through the male mold of the movable support 44. The air suction is effected through the female mold of the stationary support 42. The continuous sheet 27 as softened is tightly contacted on the female mold, to form a plurality of disk-like portions.

The hole punch/die set 30 includes a stationary support 30a and a movable support 30b. The stationary support 30a supports a die for cutting the axial hole 16a in the disk-like portion. The movable support 30b supports a punch for cutting, and is movable in a vertical direction while guided by guide shafts 30c. The movable support 30b is driven by a hydraulic cylinder, a cam or the like. Dust 47 created by the hole punch/die set 30 forming the axial hole 16a is dropped down from the die, passed through a passage 48 under the stationary support 30a, and exited through an exit 49 formed in a side of the stand 34.

Figure 4A:
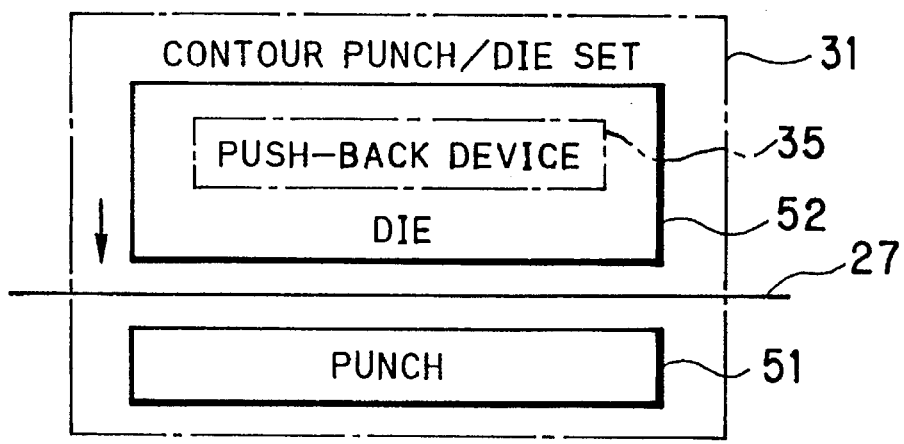
FIG. 4A is a schematic diagram illustrating the contour punch/die set with a push-back device.

The contour punch/die set 31 is constructed in fashion similar to the hole punch/die set 30, and has a stationary support 31a and a movable support 31b. In FIG. 4, the stationary support 31a supports a punch 51 for cutting the disk 16 from a disk-like portion 50 while the continuous sheet 27 is placed. The movable support 31b supports a die 52 for cutting the disk 16 and is movable in a vertical direction while guided by guide shafts 31c.

The continuous sheet 27 having the disk-like portion 50 is conveyed to a station between the stationary support 31a and the movable support 31b. The movable support 31b is moved down by a hydraulic cylinder, a cam or the like. The die 52 and the punch 51 squeeze the continuous sheet 27 to cut out the disk 16. There is disposed a push-back device 35 in FIG. 4A, which return the disk 16 to a punch hole formed by cutting the disk 16. The continuous sheet 27 is moved together with the disk 16 to the disk remover unit 32. Note that the push-back device is eliminated from FIG. 4 for simplification in convenience.

The disk 16 cut out by the contour punch/die set 31 is returned to a punch hole in the continuous sheet 27. There is occurrence of accidental rise of the disk 16 from the continuous sheet 27 as indicated by the phantom lines, when the disk 16 remains inside the die 52. Should the contour punch/die set 31 continue punching with the disk 16 unremoved, disks would come to remain in the die 52 one after another. There is a stabilizer, known in the art, for stopping the punching operation in response to detection of overload to the hydraulic cylinder, the cam or the like driving the movable support 31b. In the stop of the operation, the disk 16 deposited on the die 52 is removed either automatically or manually.

However, the disk 16 remaining in the die 52 is overlaid on another disk cut subsequently. It is likely that the overlaid two are dropped together from the die 52, sent to the disk remover unit 32, and mounted on the spool core 13. To avoid such difficulties, there is a photoelectric switch 54 of a reflection type, disposed near to the contour punch/die set 31 and directed to the die 52 of the movable support 31b. The photoelectric switch 54 includes a light projector 54a and a light receiver 54b. The light projector 54a emits an inspecting beam as electromagnetic ray to the die 52. The light receiver 54b receives the beam reflected by the die 52, and generates a voltage signal in response to a light amount of the incident beam. The voltage signal from the light receiver 54b is different between an occasion where the beam is reflected by the die 52 and an occasion where the beam is reflected by the disk 16. It is possible to check whether the disk 16 is deposited on the die 52. The voltage signal is input to a controller 55 which consists of a computer.

The controller 55 consists of a microcomputer or the like, and judges whether or not the disk 16 remains deposited to the die 52 in accordance with the voltage signal from the light receiver 54b. When the disk 16 is on the die 52, then it is judged that the disk 16 will overlie on another cut out next by the die 52. Information of the disk 16 is stored and tracked. The controller 55 also controls for the shape inspection of the disk 16 to check presence of burr and/or deposit. Note that the term "deposit" is herein used to refer to dust, dirt or other unwanted deposted material.

The disk remover unit 32 includes a sheet support 57, a disk sucker 58 and an arm 59. The sheet support 57 supports the continuous sheet 27 with the disk 16 returned. The disk sucker 58 sucks the disk 16 away from the continuous sheet 27 and keep the disk 16 raised. The arm 59 rotates the disk sucker 58 away from the sheet support 57. There is a conveyor belt 60 near to the disk remover unit 32 for conveying the disk 16 removed from the continuous sheet 27 toward a spool assembling apparatus, where the disk 16 is secured to the spool core 13. The disk sucker 58 effect air suction to the disk 16. It is also possible for a retainer device to adsorb the disk 16 electrostatically, or grasp the disk 16 mechanically without damaging the disk 16.

When the disk sucker 58 raises the disk 16, the arm 59 is rotated to move the disk sucker 58 to a position above the conveyor belt 60. The air suction caused by the disk sucker 58 is released, so that the disk 16 is placed on the conveyor belt 60. The conveyor belt 60 is moved by rotation of a roller 60b about which a belt member 60a is disposed, to convey the disk 16 toward a spool assembling apparatus. The disk 17 is also produced by a disk producing apparatus similar to that for the disk 16. After the overlay inspection is effected, the disk 17 is conveyed to the spool assembling apparatus. Note that it is possible for a single disk producing apparatus to produce the disks 16 and 17, simultaneously or alternately, to be conveyed to the spool assembling apparatus.

As illustrated in FIG. 5, the disk 16 produced by the disk producing apparatus 26 is conveyed by the conveyor belt 60 for spool assemblage. There is a shape inspector 63 in a position of the conveyor belt 60 for checking presence of burr and/or deposit on the disk 16. The shape inspector 63 includes a light source 64, a CCD (charge coupled device) camera 65, an image processor 66 and the controller 55. The light source 64 illuminates the disk 16 on the conveyor belt 60. The CCD camera 65 is a solid-state pick-up device which picks up the disk 16 one after another. The image processor 66 receives image data generated from the CCD camera 65 and converts it into measured pattern data representing density distribution of the image. A memory 55a stores reference pattern data. The controller 55 compares the measured pattern data from the image processor 66 with the reference pattern data, and evaluates the shape of the disk 16. The controller 55 is the same as used for the overlay inspection at the die 52.

The controller 55 also controls an eliminator device 68 for removing the disk 16 judged as unaccepted. When the disk 16 having an overlaid status detected to overlie on another comes to a disk removing station, or when the disk 16 detected to have an unacceptable shape comes thereto, then the controller 55 controls the eliminator device 68 to remove the disk 16 from the conveyor belt 60.

The eliminator device 68 includes a disk sucker 68a and an arm 68b. The disk sucker 68a sucks and retains the disk 16. The arm 68b moves the disk sucker 68a from the conveyor belt 60 to an exit chute 69 through which the disk 16 is abandoned. To retain the disk 16, the disk sucker 68a effects air suction, but may effect electrostatic adsorption or mechanical grasping. The disk 16 produced and conveyed consecutively is inspected for the overlay and presence of burr and/or deposits. If the disk 16 detected as unacceptable is eliminated from conveyance to the station of mounting on the spool core 13. Only the acceptable disk 16 is conveyed to the spool core 13.

Figure 6A:
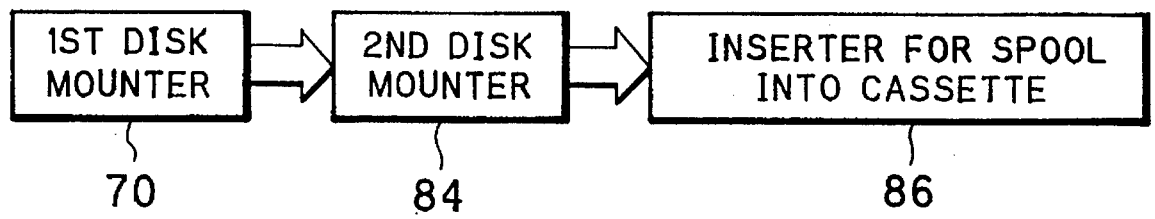
FIG. 6A is a flow chart illustrating a line from the first disk mounter to an inserter for the spool into the cassette.
Figure 6:
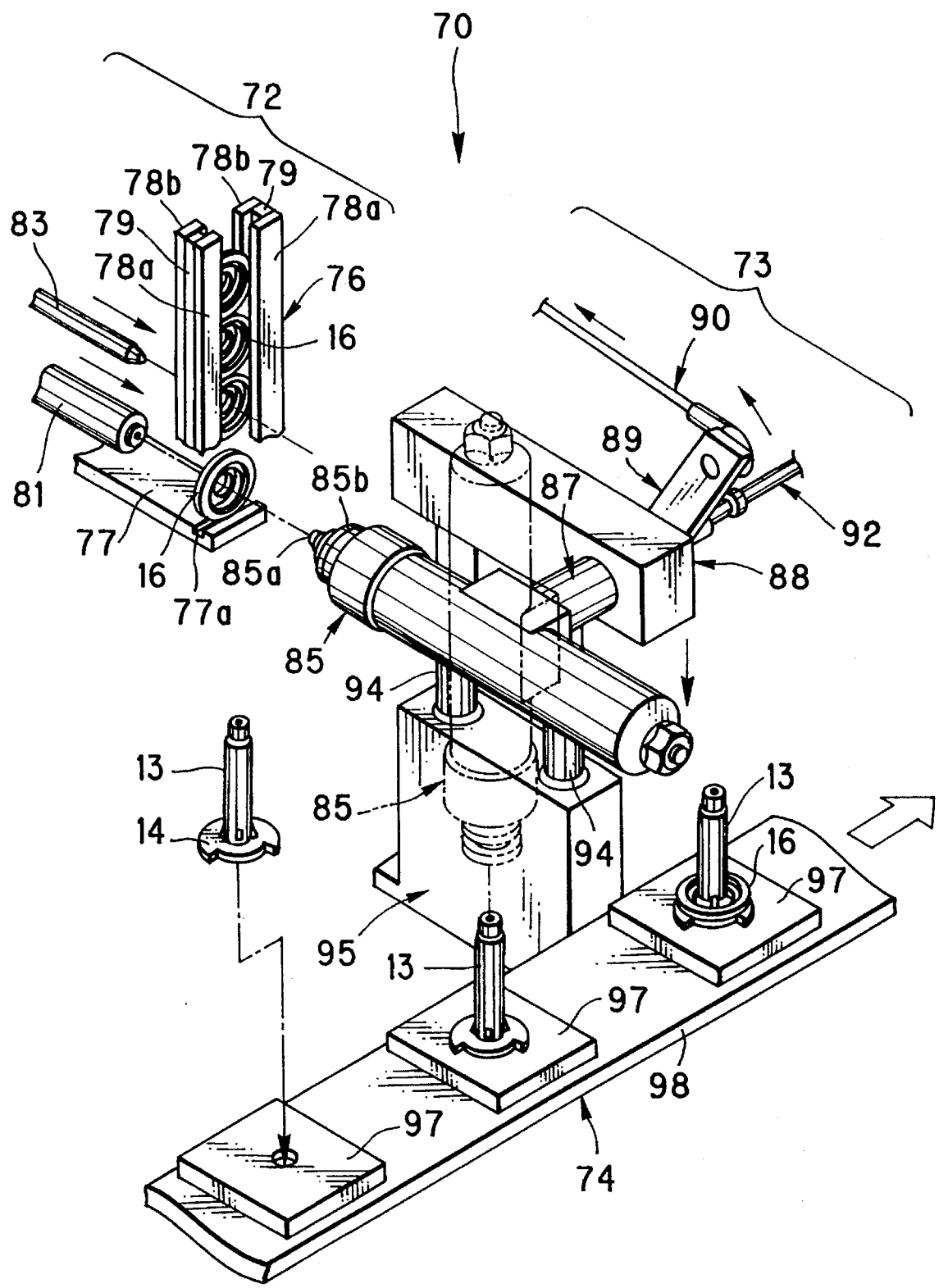
FIG. 6 is a perspective illustrating a first disk mounter in a spool assembling apparatus.

As illustrated in FIG. 6, a first disk mounter 70 in a spool assembling apparatus includes a disk supplier 72, a core/disk inserter 73 and a spool core supplier 74. The disk supplier 72 supplies the disk 16 conveyed by the conveyor belt 60. The core/disk inserter 73 retains the disk 16 and inserts the spool core 13 therein. The spool core supplier 74 supplies the spool core 13 to a disk inserting station.

The disk supplier 72 includes a supply chute 76 and a stop plate 77. After the disk 16 is conveyed by the conveyor belt 60, the disk 16 is inserted down through the supply chute 76. The stop plate 77 receives the disk 16 supplied by the supply chute 76, and positions the disk 16. The supply chute 76 includes front guide plates 78a, rear guide plates or base plates 78b and spacers 79. The front guide plates 78a are contacted on the front of the disk 16. The base plates 78b are contacted on the rear of the disk 16. The spacers 79 are located between the front guide plates 78a and the base plates 78b, and define a space enough for the disk 16 to move down. The disk 16 inserted into the top of the supply chute 76 is moved down by the gravity along the supply chute 76. The stop plate 77 has a groove 77a, which receives insertion of an edge of the disk 16 to position the disk 16.

There is a supply pin 81, disposed to confront with the disk 16 supported in the groove 77a in the stop plate 77, for removing the disk 16 and transporting the disk 16 to the core/disk inserter 73. When the disk 16 is placed on the stop plate 77, the supply pin 81 is moved in the arrow direction by a motor, an air cylinder, a solenoid, a cam or the like, and retains the disk 16 in the air suction. The supply pin 81 is further moved with the disk 16, and conveys the disk 16 to the core/disk inserter 73.

A stopper pin 83 is disposed over the supply pin 81. When the disk 16 is moved down to the stop plate 77 from the supply chute 76, the stopper pin 83 is moved in the arrow direction by a motor, an air cylinder, a solenoid, a cam or the like. Then the stopper pin 83 is inserted in the axial hole 16a in the disk 16 above the stop plate 77. Accordingly the disk 16 is kept from dropping down to the stop plate 77 before a preceding disk on the stop plate 77 finishes being moved to the core/disk inserter 73.

The supply pin 81 with the disk 16 is thrust toward the core/disk inserter 73, and supplies the disk 16 for an inserter holder 85 disposed in a moving path of the supply pin 81. The inserter holder 85 includes a centering pin 85a and a holder ring 85b. The centering pin 85a is inserted into the axial hole 16a in the disk 16, and positions the disk 16 during assemblage for the spool core 13. The holder ring 85b is shaped for contact on the disk 16.

The inserter holder 85 has a rotational shaft 87 which is projected therefrom in a horizontal direction, and supported through a holder support 88 in rotatable fashion. An axial end of the rotational shaft 87 behind the holder support 88 has one end of a lever 89. Another end of the lever 89 is secured to a connector rod 90. When the connector rod 90 is pulled in the arrow direction as shown, the lever 89 is rotated counterclockwise. The inserter holder 85 rotates counterclockwise together. As indicated by the phantom lines, the holder ring 85b of the inserter holder 85 is directed downward.

An air hose 92 is connected to a hole formed in the rotational shaft 87 through the holder support 88. There is an air pump connected to the air hose 92. An air path is formed through the rotational shaft 87, and connected between the air hose 92 and an air path formed in the inserter holder 85. The air pump upstream from the air hose 92 effects air suction through the holder ring 85b, to retain the disk 16. Note that the air hose 92 is secured in rotatable fashion relative to the rotational shaft 87, and is not twisted when the inserter holder 85 is rotated.

The holder support 88 has two guide shafts 94, which are inserted in slidable fashion in a holder support 95 disposed under the holder support 88. The holder support 88 is slid in a vertical direction while guided by the holder support 95, by use of a motor, an air cylinder, a solenoid, a cam or the like. Accordingly, the inserter holder 85 receives the disk 16 from the supply pin 81, supports it on the holder ring 85b, rotates about the rotational shaft 87, slides down while guided by the holder support 95, so as to convey the disk 16 to the inserting position.

Under the inserter holder 85 is disposed the spool core supplier 74. The spool core supplier 74 includes a pallet 97 and a conveyor belt 98 known in the art. The end of the spool core 13 on the side of the data plate 14 is inserted in a hole of the pallet 97, which is placed on the conveyor belt 98, and conveyed intermittently thereby to a disk inserting station. The spool core 13 on the pallet 97 is moved to, and stopped in, a position under the inserter holder 85 directed downward. After receiving insertion of the disk 16, the conveyor belt 98 is driven again to convey the spool core 13 to a second disk mounter 84 in FIG. 6A, where the disk 17 receives insertion of the spool core 13.

To insert the spool core 13 into the disk 16, the inserter holder 85 with the disk 16 is rotated by the rotational shaft 87, to direct the holder ring 85b downward. The holder support 88 is moved down while guided by the holder support 95. With the inserter holder 85 moved down, the centering pin 85a is inserted into a top end of the spool core 13. The inserter holder 85 is further moved down. The centering pin 85a is pushed by the spool core 13, and pressed back into the inserter holder 85. The disk 16 is mounted on the spool core 13 near to the data plate 14 while pressed by the holder ring 85b.

The inserter holder 85 is stopped from effecting the air suction, and is returned to the initial position to receive the disk 16 from the supply pin 81. The spool core 13 provided with the disk 16 closer to the data plate 14 is conveyed to the second disk mounter 84 where the disk 17 is secured. The second disk mounter 84 for the disk 17 is substantially the same as that for the disk 16. The second disk mounter 84 for the disk 17 is different only in the shapes of the supply pin and the inserter holder, and the downward stroke of the inserter holder.

Figure 7:
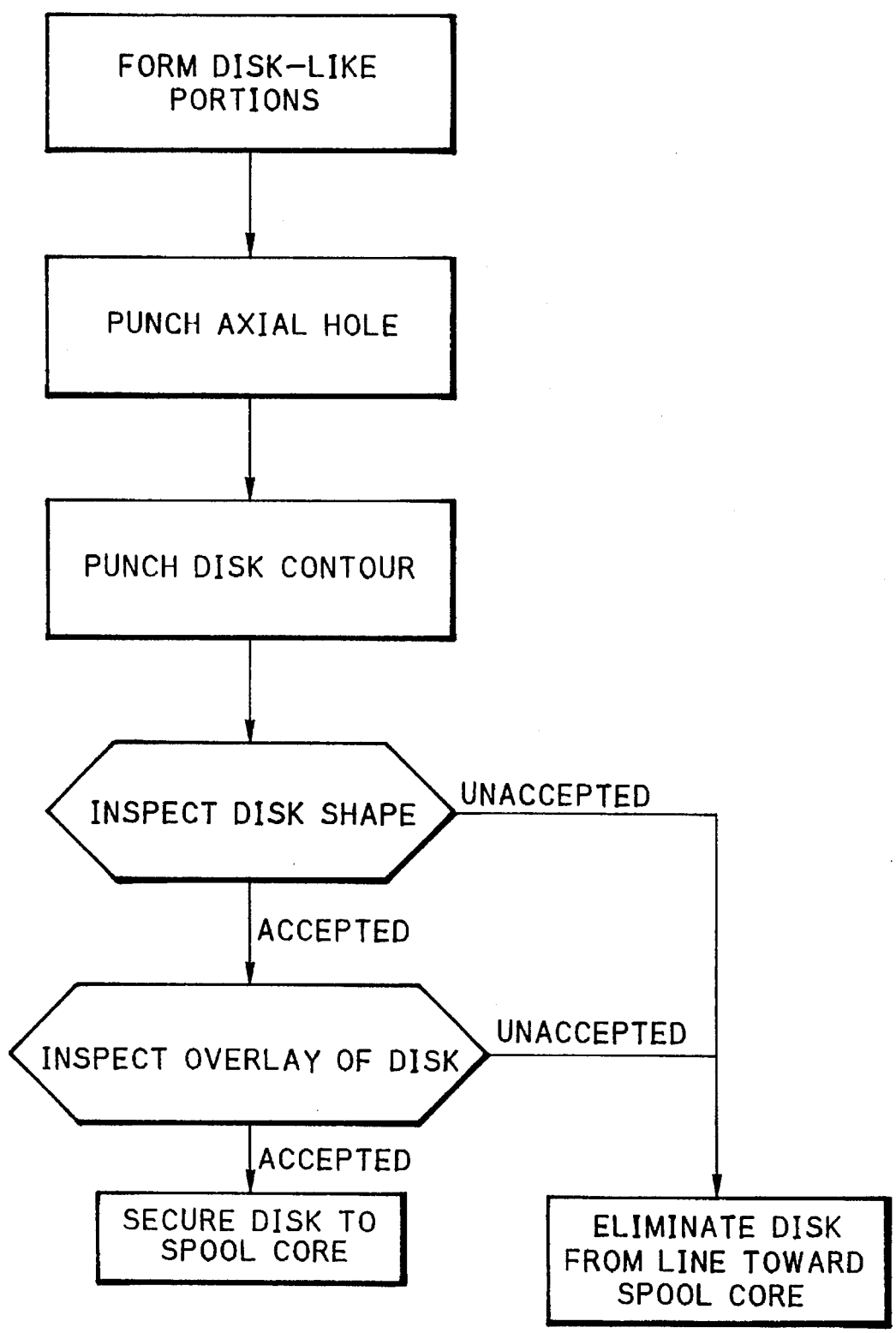
FIG. 7 is a flow chart illustrating disk inspecting processes of the present invention.

Operation of the above constructed preferred embodiment is described with reference to FIG. 7. In the disk producing apparatus 26 in FIG. 3, the continuous sheet 27 is supplied by the sheet supply unit 28 to the forming unit 29, where the sheet heater 45 is inserted between the stationary support 42 and the movable support 44, and heats the softens the continuous sheet 27. After heating the continuous sheet 27, the sheet heater 45 is retracted from between the stationary support 42 and the movable support 44, before the movable support 44 is moved down to the stationary support 42.

During the downward movement of the movable support 44, the air pressurization is effected through the male mold of the movable support 44. The air suction is effected through the female mold of the stationary support 42. The continuous sheet 27 is tightly contacted on the female mold, to form a plurality of the disk-like portion 50 (See FIG. 4) on the continuous sheet 27.

The continuous sheet 27 with the disk-like portion 50 is conveyed into the hole punch/die set 30, to cut the axial hole 16a. The continuous sheet 27 with the axial hole 16a is conveyed to the contour punch/die set 31 in FIG. 4 and between the stationary support 31a and the movable support 31b, and placed on the punch 51 of the stationary support 31a. Then the movable support 31b is moved down to the stationary support 31a. The punch 51 and the die 52 come to confront with to each other, to cut the contour of the disk-like portion 50, to shape the disk 16. The movable support 31b after punching of the disk 16 from the continuous sheet 27 is moved up. The disk 16 is returned to the punch hole by the push-back device 35.

When the movable support 31b is raised, the photoelectric switch 54 near to the contour punch/die set 31 applies an inspecting beam to the die 52 through the light projector 54a. The inspecting beam is reflected by the die 52 or the disk 16 remaining in the die 52, and comes incident upon the light receiver 54b. The light receiver 54b supplies the controller 55 with a voltage signal in accordance with the incident beam as reflected from the die 52 or the disk 16. The controller 55 evaluates the signal, and determines whether the disk 16 is deposited on the die 52. If it is, then information of the disk 16 is stored in the memory 55a and tracked.

The disk 16 cut out by the contour punch/die set 31 is conveyed to the disk remover unit 32 by movement of the continuous sheet 27. The disk sucker 58 of the disk remover unit 32 effects the air suction and removes the disk 16 from a punch hole in the continuous sheet 27 placed in the sheet support 57. The arm 59 moves the disk sucker 58 to the conveyor belt 60. Then the air suction of the disk sucker 58 is stopped, to place the disk 16 on the belt member 60a.

The conveyor belt 60 conveys the disk 16 on the belt member 60a to the first disk mounter 70 in rotation of the roller 60b. In FIG. 5, the light source 64 of the shape inspector 63 illuminates the disk 16, which is picked up by the CCD camera 65. The image data from the CCD camera 65 is converted by the image processor 66 into the measured pattern data representing the density distribution. The measured pattern data is compared with the reference pattern data written to the memory 55a. The controller 55 evaluates the shape of the disk 16 according to a compared result, to determine acceptance of the disk 16.

The disk 16 unaccepted according to the shape inspection and the overlay inspection is eliminated from the conveyor belt 60 by the eliminator device 68 controlled by the controller 55. The disk sucker 68a of the eliminator device 68 raises the disk 16. The arm 68b rotates to move the disk 16 to a position over the exit chute 69, where the disk 16 is dropped. The disk 16 to be supplied to the first disk mounter 70 is acceptable among ones conveyed by the conveyor belt 60.

The disk 16 conveyed by the conveyor belt 60 is supplied into the supply chute 76 of the disk supplier 72 in FIG. 6. The disk 16 moved down inside the supply chute 76 by gravity is supplied to the stop plate 77 and supported by the groove 77a. The supply pin 81 starts being moved in the arrow direction by the motor, the air cylinder, the solenoid, the cam or the like.

The supply pin 81 effects the air suction of the disk 16 placed on the stop plate 77, and moved toward the core/disk inserter 73 with the disk 16. In movement of the disk 16 on the supply pin 81, the stopper pin 83 over the supply pin 81 is also moved in the arrow direction, to receive the axial hole 16*a* in a lowest one of the disks 16 inside the supply chute 76. It is possible during horizontal movement of the disk 16 to the core/disk inserter 73 to avoid dropping succeeding ones of the disk 16 through the supply chute 76.

In the moving path of the supply pin 81, the inserter holder 85 of the core/disk inserter 73 is standing by. The disk 16 is transferred from the supply pin 81 to the inserter holder 85. The inserter holder 85 inserts the centering pin 85*a* into the axial hole 16*a* in the disk 16. The air suction is effected through the holder ring 85*b* to retain the disk 16. After the transfer of the disk 16 from the supply pin 81 to the inserter holder 85, the supply pin 81 returns to an initial position leftward along the stop plate 77.

When the inserter holder 85 captures the disk 16, the connector rod 90 is pulled in the arrow direction by the motor, the air cylinder, the solenoid, the cam or the like. The lever 89 is rotated in the counterclockwise direction. So is the inserter holder 85. The end capturing the disk 16 is directed downward.

Under the inserter holder 85 is disposed the spool core supplier 74 where the conveyor belt 98 conveys the spool core 13 with the pallet 97. When the spool core 13 is stopped in the disk inserting station, the shape inspector 63 is guided by the guide shafts 94 and moved down by the motor, the air cylinder, the solenoid, the cam or the like. The inserter holder 85 is moved down.

When the inserter holder 85 comes down, the centering pin 85*a* abuts on the top end of the spool core 13. The inserter holder 85 is further moved down. The centering pin 85*a* is pushed into the inserter holder 85. The disk 16 pushed by the holder ring 85*b* is mounted on the spool core 13 and near to the data plate 14. Then the inserter holder 85 stops the air suction, and returns to the initial position for receiving the disk 16 from the supply pin 81. The spool core 13 provided with the disk 16 is conveyed to the second disk mounter 84 for insertion of the disk 17, to obtain the spool 5, which is conveyed to an inserter 86 for including the 5 into the cassette, and inserted between the upper and lower shell halves 3 and 4. The photo film cassette is finally produced.

Figure 8:
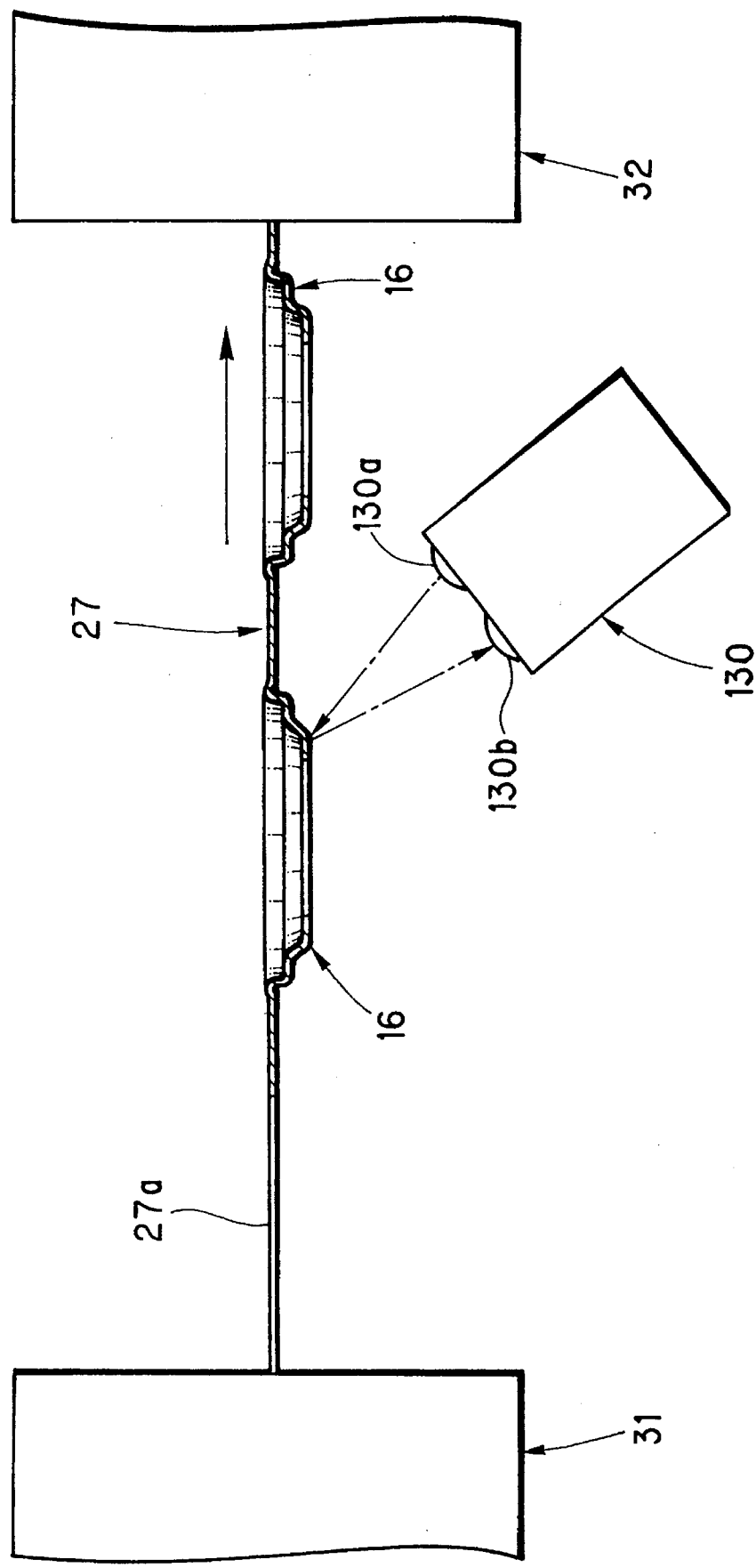
FIG. 8 is an explanatory view illustrating another preferred process of disk overlay inspection where a punch hole is photoelectrically checked.

Note that the deposition of the disk 16 to the die 52 is directly detected by the photoelectric switch 54 in the above embodiment. Alternatively a photoelectric switch 130 of a reflective type in FIG. 8 may be disposed under the continuous sheet 27 between the contour punch/die set 31 and the disk remover unit 32.

The photoelectric switch 130 includes a light projector 130*a* and a light receiver 130*b*. The light projector 130*a* emits an inspecting beam to the continuous sheet 27. The light receiver 130*b* receives the beam reflected by the disk 16 in a punch hole 27*a* or sheet portions about the punch hole 27*a*, and generates a voltage signal in response to a light amount of the incident beam. If the beam is reflected by the continuous sheet 27 or the disk 16, then the light receiver 130*b* generates the voltage signal of a positive value. If the beam is applied to the punch hole 27*a* without the disk 16, then the voltage signal from the light receiver 130*b* is zero volt. It is possible to detect absence of the disk 16 in the punch hole 27*a*.

The signal generated by the light receiver 130*b* is entered to the controller 55 (See FIG. 5). It is possible to determine whether the disk 16 is overlaid on another when returned into the punch hole 27*a* of a position upstream as much as a range of plural disks, as well as the inspection of deposition of the disk 16 on the die 52. The lapped disks can be abandoned by the eliminator device 68 together with disks of unaccepted shapes. Note that it is possible in detection of the disk 16 in the punch hole 27*a* to use a transmission type of photoelectric switch instead of the photoelectric switch 130. The transmission type includes a light projector and a light receiver, between which the continuous sheet 27 is passed.

Figure 9:
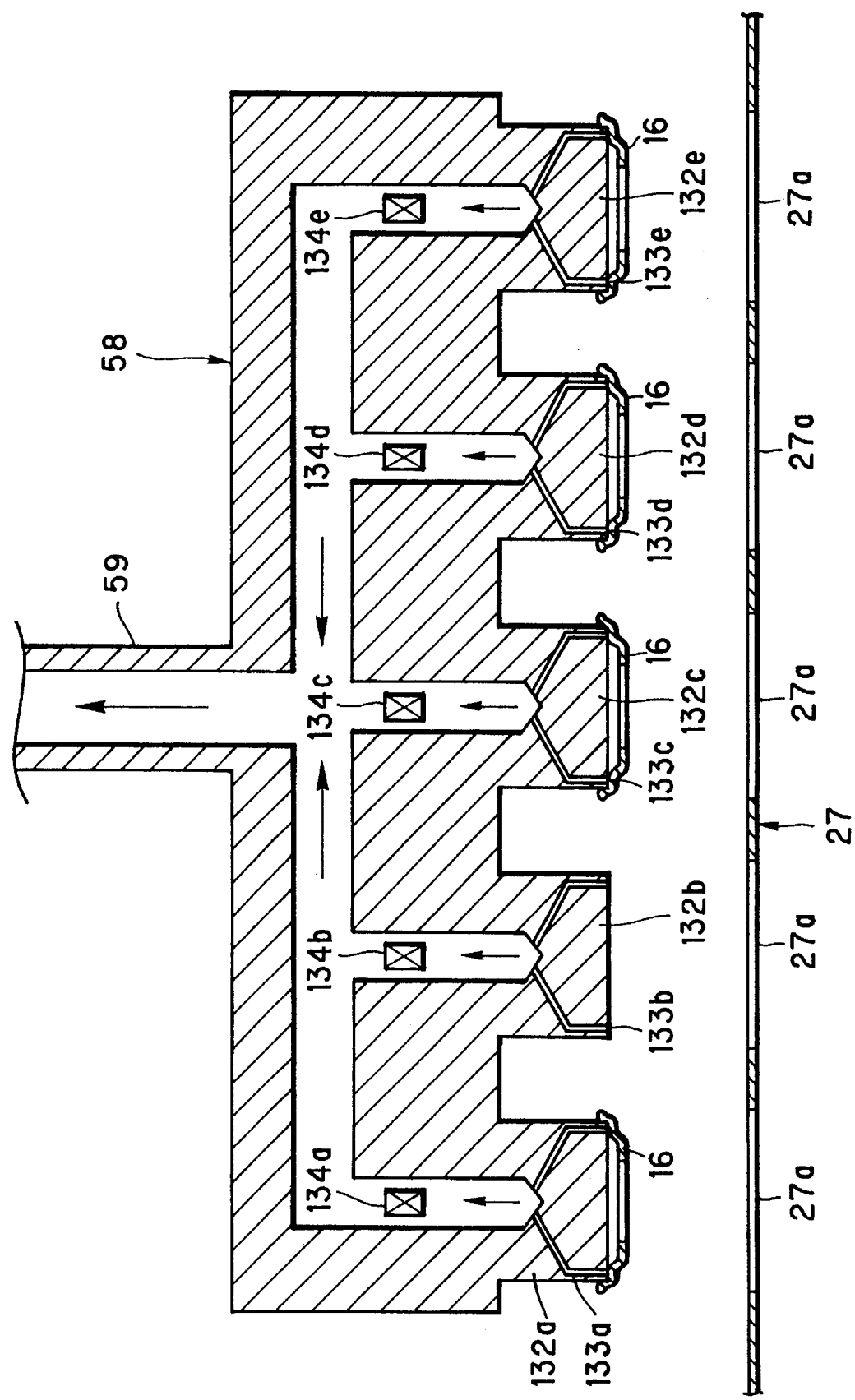
FIG. 9 is an explanatory view illustrating a further preferred process of disk overlay inspection where sucking pressure in disk removal is checked.

Further it is possible to detect presence/absence of the disk 16 returned into the punch hole 27*a* before removing the disk 16 therefrom. This operation is effected in the disk remover unit 32. In FIG. 9, the disk sucker 58 has disk sucker pads 132*a*–132*e*. There are pressure switches 134*a*–134*e* respectively disposed inside the disk sucker pads 132*a*–132*e* for measuring pressure sucking the disk 16.

If the disk 16 does not exists under the disk sucker pad 132*b* for example, there is no change in a measured value at the pressure switch 134*b* associated with the disk sucker pad. It is possible to detect absence of the disk 16 in the punch hole 27*a* located under the disk sucker pad 132*b*, and similarly, under any of the disk sucker pads 132*a*–132*e*. Outputs of the pressure switches 134*a*–134*e* are entered to the controller 55 (See FIG. 5). It is possible to determine if the disk 16 is overlaid on another when returned into the punch hole 27*a* of a position upstream as much as a range of plural disks, as well as the inspection of deposition of the disk 16 on the die 52. The lapped disks can be abandoned by the eliminator device 68 together with disks of unaccepted shapes. Note that the disk sucker pads 132*a*–132*e* have respective sucking holes 133*a*–133*e* which have a reduced diameter to heighten sucking pressure. If one of the disk sucker pads does not suck any disk, the one pad does not affect the sucking pressure of the other of the pads.

It is also possible to use the shape inspector 63 for the overlay inspection: when the disk 16 is supplied from the disk remover unit 32 to the conveyor belt 60 consecutively one after another, the shape inspector 63 may be directed to a train of the disks, to check a position where the disk 16 is absent. It is possible to detect the overlay of the disk 16 in a position upstream as much as a range of a plurality of disks.

Figure 10:
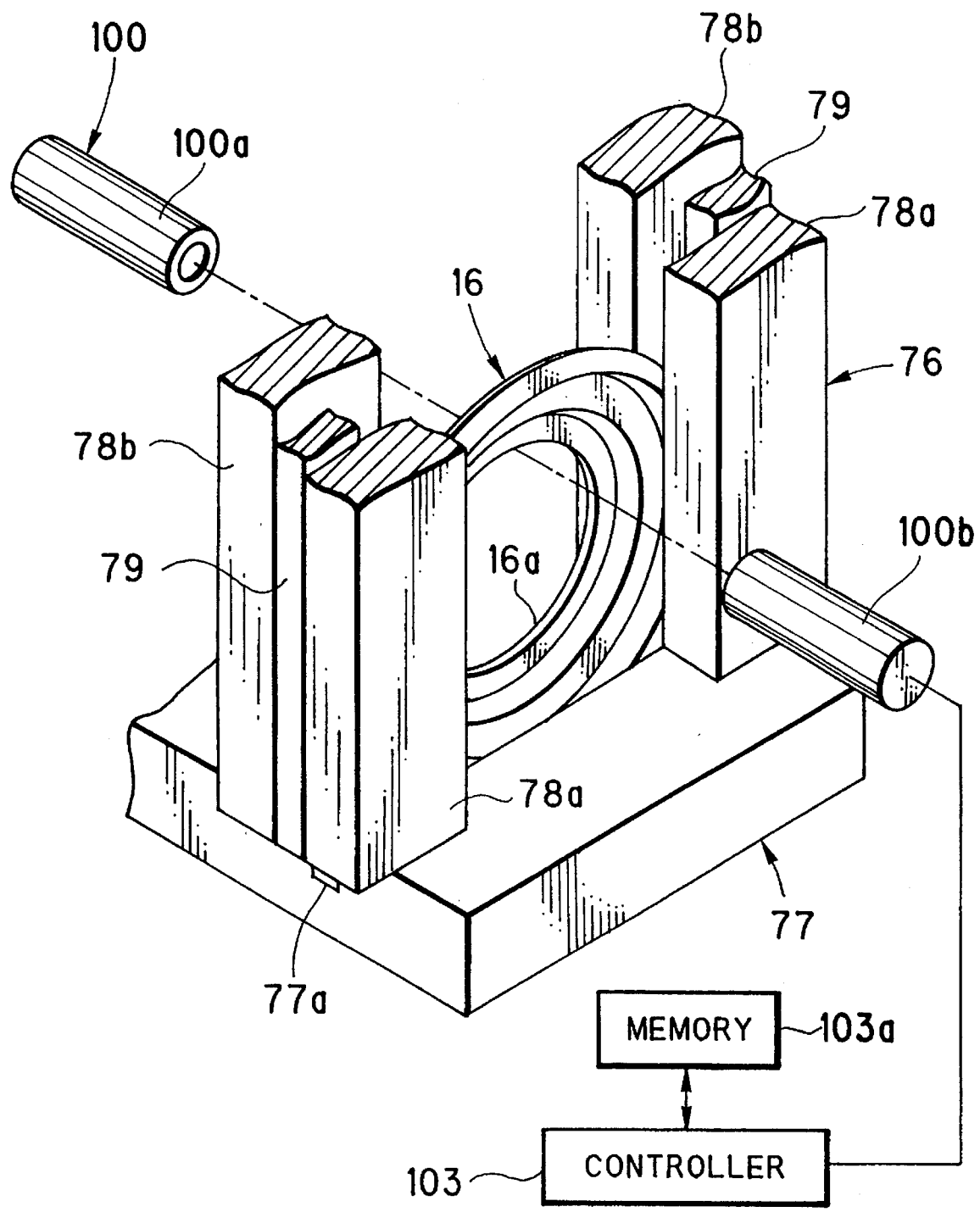
FIG. 10 is a perspective illustrating still another preferred process of disk overlay inspection where optical transmittance of each disk is checked.

For the overlay inspection of the disk 16, other methods hereinafter described can be used. FIG. 10 illustrates an embodiment in which optical transmittance of the disk 16 is utilized for the overlay inspection in the position of the supply chute 76.

Near to the supply chute 76 is disposed a photoelectric switch 100 of a transmission type which includes a light projector 100*a* and a light receiver 100*b*, between which the disk 16 in the supply chute 76 is passed. The light projector 100*a* applies an inspecting beam to the disk 16 in convergency at a diameter of 0.2 mm. The beam-applied position to which the light projector 100*a* is directed is determined around the axial hole 16*a* of the disk 16, namely where overlay of two disks may be inevitably detectable. If the disk 17 is desired to be inspected, the beam-applied position is determined around the axial hole 17*a* and also around the arc-like slits 23. Portions 101 in FIG. 2C are excluded.

The inspecting beam from the light projector 100*a* is transmitted through the disk 16 and received by the light receiver 100*b*. The light receiver 100*b* generates a voltage signal in response to a light amount of the incident beam. The voltage signal is input to a controller 103 which consists of a computer. The light projector 100a and the light receiver 100b were experimentally adjusted: when nothing is located between the light projector 100a and the light receiver 100b, the light receiver 100b was caused to generate a voltage signal of zero volt. When the light receiver 100b was completely intercepted from the light projector 100a, the light receiver 100b was caused to generate a voltage signal of 3–4 volts. The disk 16 is translucent. A threshold value for the overlay inspection depends on transmittance of the disk 16 formed of certain material. The threshold value was experimentally set 1.5 volts and stored in a memory 103a. If the output signal from the light receiver 100b is 1.5 volts or lower, the controller 103 judges that the disk 16 is single without any other disk overlaid. If the output signal from the light receiver 100b is higher than 1.5 volts, there is another disk overlaid on the disk 16.

Figure 11:
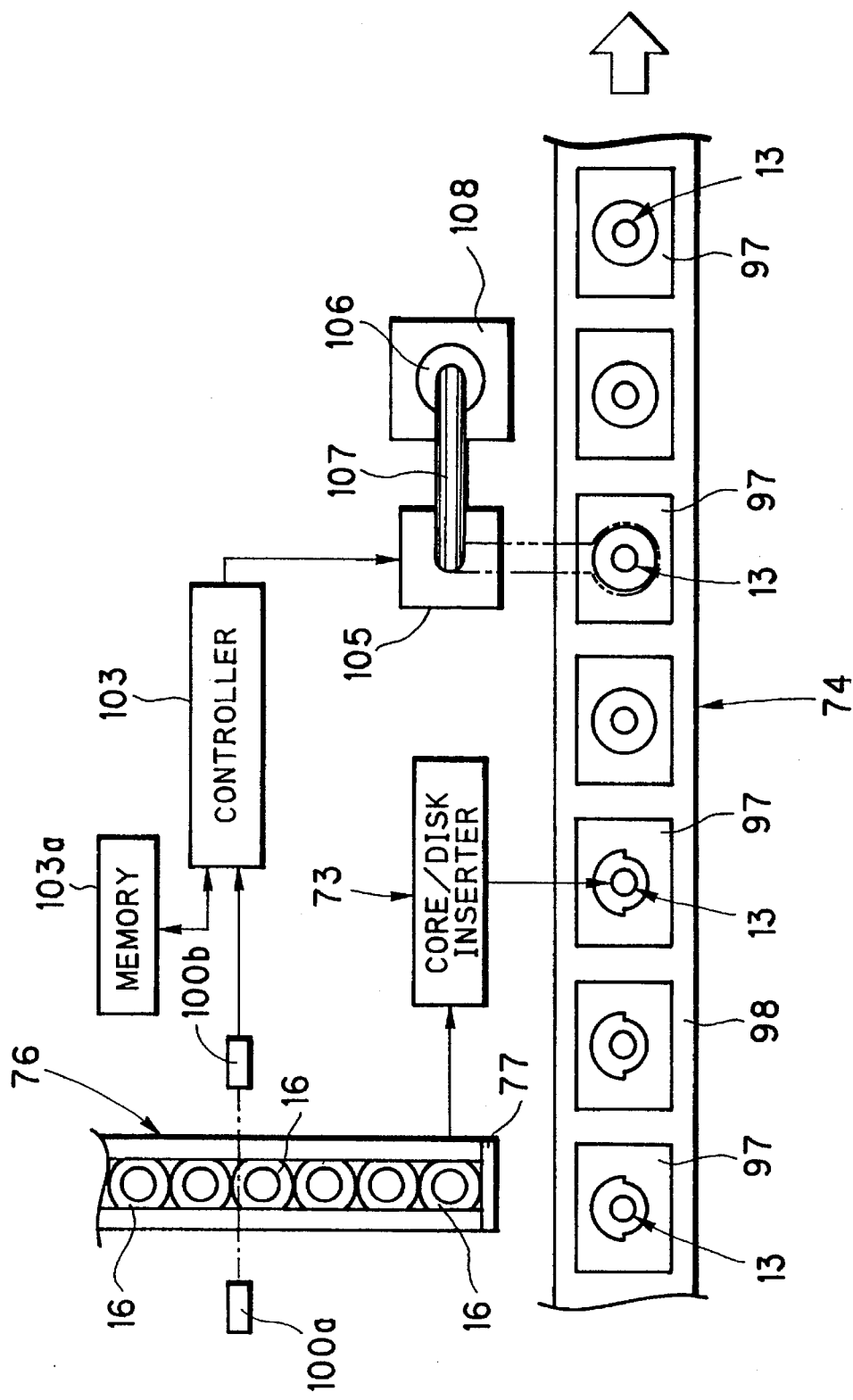
FIG. 11 is an explanatory view illustrating the process of FIG. 10 together with a disk eliminator device.

The controller 103 controls an eliminator device 105 of FIG. 11 disposed beside the spool core supplier 74. If the spool core 13 is tracked and judged as having the disk 16 overlaid on another, the spool core 13 is eliminated from the pallet 97. The eliminator device 105 includes a spool sucker 106 and an arm 107. The spool sucker 106 raises the spool core 13. The arm 107 rotates the spool sucker 106. The spool core 13 with an unacceptable disk 16 is moved to and dropped into an exit chute 108.

Figure 12A:
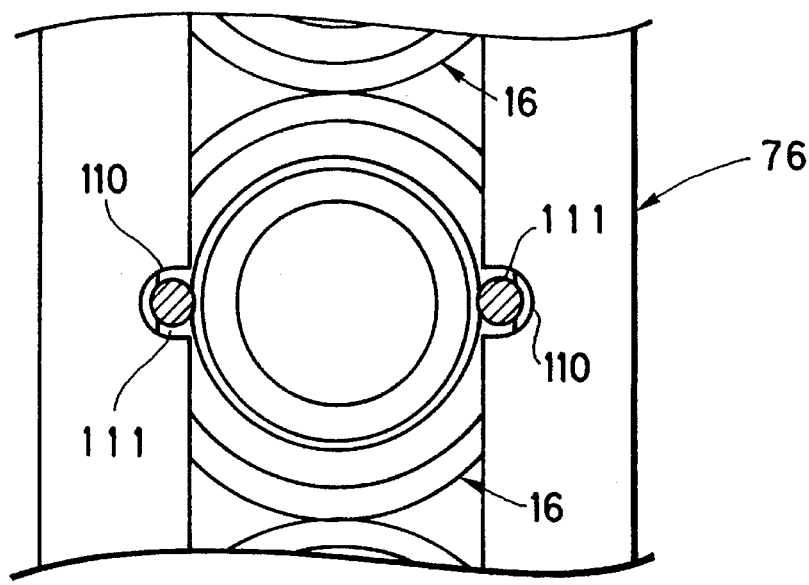
FIG. 12A is an explanatory view in elevation, illustrating an additional preferred process of disk overlay inspection in which disk thickness is optically measured and checked.
Figure 12B:
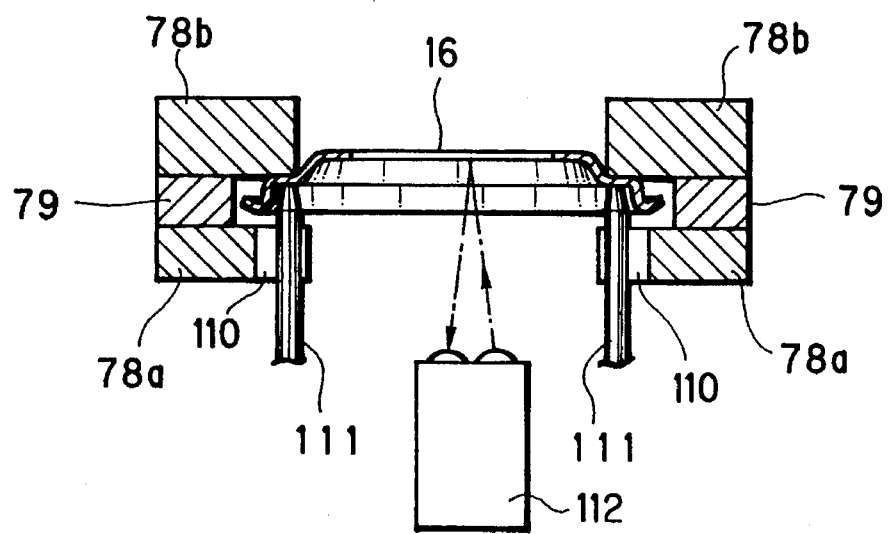
FIG. 12B is an explanatory view in section, illustrating the process of FIG. 12A together with a rangefinder.
Figure 13:
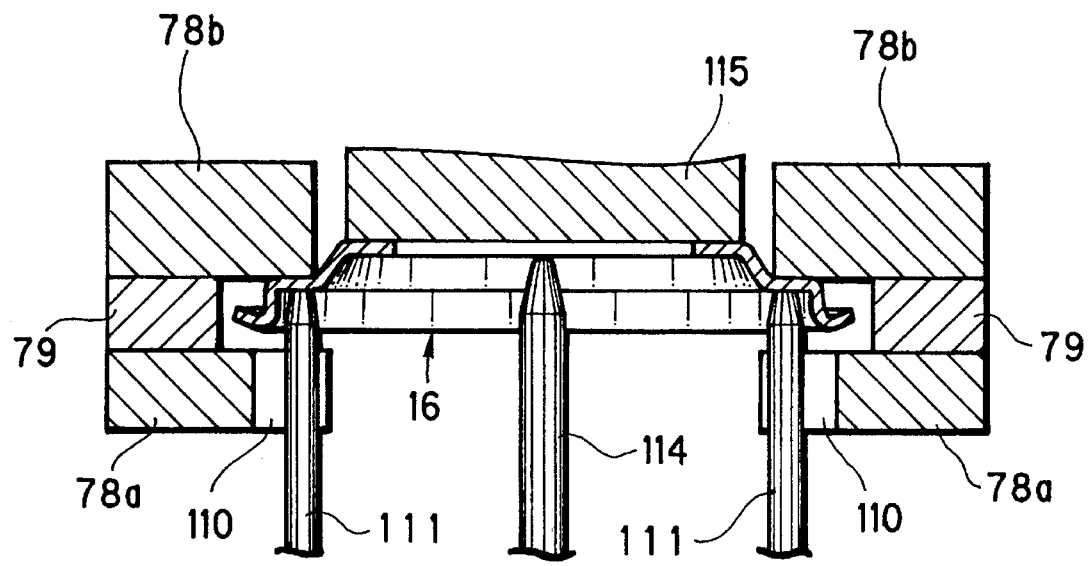
FIG. 13 is a cross section illustrating still another preferred process of disk overlay inspection in which disk thickness is mechanically measured and checked.

FIGS. 12A and 12B illustrate still another preferred embodiment in which thickness of the disk 16 is measured and checked for the overlay inspection. Cutouts 110 are formed in the front guide plates 78a of the supply chute 76. Push-pins 111 are inserted through the cutouts 110, and press the disk 16 against the base plates 78b. For advancing motion of the pushpins 111, an air cylinder, a cam or the like is used. It is possible not to use the pushpins 111, but to blow air over the disk 16 for pressing the disk 16 against the base plates 78b.

An optical rangefinder 112 measures distance to a surface of the disk 16, to obtain thickness of the disk 16 with another disk which may be overlaid thereon. For example, the optical rangefinder 112 projects a laser beam and receives it after reflection on the disk 16. Alternatively it is possible to use a three-dimensional measuring machine including a base plate 115 and a probe 114. The upper face the disk 16 is contacted on the base plate 115, while the probe 114 is contacted on the lower face of the disk 16 to measure the thickness by monitoring a position of the probe 114 relative to the base plate 115. Note that the incident position of the inspecting beam of the optical rangefinder 112 and the contact position of the probe 114 can be determined around the axial hole 16a, namely where overlay of two disks may be inevitably detectable. Those inspecting methods are effective when material of the disk 16 has high reflectivity. Those are effective also if the disk 16 is transparent or translucent.

FIG. 14 illustrates a preferred embodiment in which weight of the disk 16 is measured and checked for the overlay inspection. There is a conveying path 119 for the disk 16 from the disk producing apparatus to the spool assembling apparatus. There are disposed a weighting device 117, a guide plate 118 and gate plates 120. The guide plate 118 has a small weight, and is mounted on the weighting device 117. The gate plates 120 intercept the conveying path 119 from the guide plate 118.

In operation, when the disk 16 conveyed through the conveying path 119 comes to the guide plate 118, the gate plates 120 are closed. The weighting device 117 measures the weight of the disk 16 on the guide plate 118. If the weight as measured is as much as one disk, the gate plates 120 are reopened to transfer the disk 16 to the conveying path 119. If the weight as measured is more than one disk, the disk 16 is removed upward away from the guide plate 118. This embodiment is effective for the overlay inspection and also for inspection of unwanted deposit on the disk 16, as the deposit would raise the weight of the disk 16.

Figure 15:
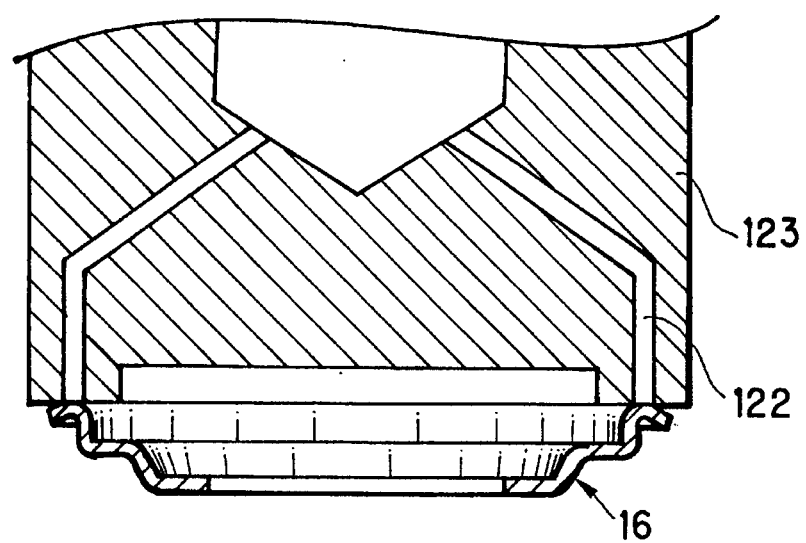
FIG. 15 is an explanatory view illustrating still another preferred process of disk overlay inspection in which only disks without overlay of any other disk are sucked and conveyed.

FIG. 15 illustrates another preferred embodiment of an overlay inspecting method, in which weight of one or two disk is considered. Elements similar to those of the above embodiments are designated with identical reference numerals. In FIG. 15, a movable conveyor plate has an air path 122 in its bottom. The peripheral portion of the disk 16 is sucked through the air path 122 by a disk sucker 123 including a pump, at a small sucking force. To be precise, the sucking force of the disk sucker 123 is sufficient for sucking up the single disk 16, but short of sucking up two disks. When the disk sucker 123 manages to raise the disk 16, the disk 16 is regarded as not overlaid with any other disk. When the disk sucker 123 does not manage to raise the disk 16, the disk 16 is regarded as overlaid with another disk.

When the disk 16 cannot be sucked and raised, the disk 16 is left to drop down, and abandoned. When the disk 16 can be raised, then the sucking force is increased, to convey the disk 16 to the spool producing apparatus. It is rendered reliable to eliminate unacceptable disks. Note that the sucking force of the disk sucker 123 is set small. It is desired that a pressure sensor monitors the sucking pressure and the retaining pressure, to check reliability of the sucking operation.

In the above embodiments, the air suction is used for elimination of unaccepted disks. Alternatively it is possible to use air blowing, brushing away, or the like to eliminate the disks. It is also possible to use two conveyor belts branched off for accepted and unaccepted disks. Further the disk overlay can be inspected by monitoring a flexed force or flexed amount of the disk. Any plural ones of the above-described method for the overlay inspection can be combined with one another in a suitable manner.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A method of inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set; said disk being returned to a punch hole formed in said disk and conveyed with said sheet; said disk being removed from said punch hole by a disk remover unit before conveyance to a spool core mounting station; said flexible disk inspecting method comprising:

a first inspecting process of inspecting a shape of said disk, to detect said disk acceptable or unacceptable; and/or a second inspecting process of inspecting occurrence of overlay of said disk on another disk before said spool core mounting station, to detect said disk unacceptable if said overlay occurs.

2. A flexible disk inspecting method as defined in claim 1, where said first inspecting process detects said disk unacceptable if said disk has burr and/or deposit, and/or is defective.

3. A flexible disk inspecting method as defined in claim 1, further comprising an eliminating process which includes steps of:

storing information identifying said disk detected unacceptable; and after said first and/or second inspecting process, eliminating said unacceptable disk before said spool core mounting station in accordance with said identifying information.

4. A flexible disk inspecting method as defined in claim 1, further comprising an eliminating process which includes steps of:

storing information identifying said disk detected unacceptable; and eliminating said unacceptable disk and said spool core after said spool core mounting station from a path toward a succeeding assembling station in accordance with said identifying information.

5. A flexible disk inspecting method as defined in claim 1, wherein said first inspecting process includes steps of:

previously storing reference information;

measuring said shape of said disk before said spool core mounting station, to obtain disk information;

comparing said disk information with said reference information, said disk being detected unacceptable if said disk information is different from said reference information.

6. A flexible disk inspecting method as defined in claim 5, wherein said first inspecting process includes steps of:

picking up said disk to obtain image data; and producing measured pattern data from said image data to represent density distribution of said disk by way of said disk information.

7. A flexible disk inspecting method as defined in claim 1, wherein said second inspecting process includes steps of:

measuring said punch/die set and/or said punch hole subsequent to returning said disk before said spool core mounting station, to obtain measured information;

detecting occurrence of deposition of said disk on said punch/die set in accordance with said measured information; and if said deposition occurs, considering said disk unacceptable due to said overlay on one subsequent disk.

8. A flexible disk inspecting method as defined in claim 7, wherein said measuring step comprises:

applying an electromagnetic ray to a blade of said punch/die set; and measuring said electromagnetic ray reflected by said blade, to obtain said measured information.

9. A flexible disk inspecting method as defined in claim 7, wherein said measuring step comprises checking existence of said disk in said punch hole, and if said disk does not exist, said disk being detected deposited on said punch/die set, and considered unacceptable due to said over-lay on one subsequent disk cuttable by said punch/die set.

10. A flexible disk inspecting method as defined in claim 9, wherein said measuring step comprises:

applying an electromagnetic ray to said sheet in a station downstream from said sheet relative to conveyance of said punch/die set;

measuring said electromagnetic ray from said sheet, to obtain said measured information.

11. A flexible disk inspecting method as defined in claim 1, wherein said disk remover unit includes a sucker, disposed over said sheet, for sucking said disk from said punch hole in air suction; and said second inspecting process includes a step of measuring sucking pressure of said sucker during said air suction, and if said sucking pressure is zero, said disk being detected not existing in said punch hole.

12. A flexible disk inspecting method as defined in claim 1, wherein said disk is translucent;

said second inspecting process includes steps of:

applying an electromagnetic ray to said disk conveyed serially after removal from said punch hole;

detecting said electromagnetic ray transmitted through said disk; and comparing transmitted intensity of said electromagnetic ray with a predetermined threshold value, and if said transmitted intensity is lower than said threshold value, said disk being detected unacceptable due to said overlay.

13. A flexible disk inspecting method as defined in claim 1, wherein said second inspecting process includes steps of:

measuring thickness of said disk; and comparing said thickness with a predetermined limit value, and if said thickness is greater than said limit value, said disk being detected unacceptable due to said overlay.

14. A flexible disk inspecting method as defined in claim 13, wherein said second inspecting process includes steps of:

contacting a base plate on a first face of said disk conveyed serially after removal from said punch hole;

optically measuring a distance from a rangefinding position to a second face of said disk reverse to said first face, said rangefinding position being predetermined opposite to said base plate with reference to said disk; and obtaining thickness of said disk from a position of said base plate, said rangefinding position and said distance measured.

15. A flexible disk inspecting method as defined in claim 13, wherein said second inspecting process includes steps of:

contacting a base plate on a first face of said disk conveyed serially after removal from said punch hole;

contacting a probe on a second face of said disk reverse to said first face;

detecting positions of said base plate and said probe; and obtaining thickness of said disk from said positions of said base plate and said probe.

16. A flexible disk inspecting method as defined in claim 1, wherein said second inspecting process includes steps of:

measuring weight of said disk; and comparing said weight with a predetermined limit value, and if said weight is greater than said limit value, said disk being detected unacceptable due to said overlay.

17. A flexible disk inspecting method as defined in claim 1, wherein a movable conveyor plate is disposed over said disk conveyed serially after removal from said punch hole;

an air path is formed to open in a bottom of said conveyor plate;

said second inspecting process includes steps of:

sucking said disk to said bottom of said conveyor plate through said air path at a sucking force short of two times as much as weight of said disk; and moving said conveyor plate during sucking operation, to allow dropping said disk unacceptably overlaid on another disk without further conveyance.

18. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set before conveyance to a spool core mounting station; said flexible disk inspecting apparatus comprising:

a measuring device, disposed upstream from said spool core mounting station, for measuring a shape of said disk to obtain disk information;

a memory for previously storing reference information; and a detector device for comparing said disk information with said reference information read from said memory, so as to detect said disk unacceptable if said disk information is different from said reference information.

19. A flexible disk inspecting apparatus as defined in claim 18, wherein said disk is returned to a punch hole formed in said disk and conveyed with said sheet, and said disk is removed from said punch hole by a disk remover unit before conveyance to said spool core mounting station.

20. A flexible disk inspecting apparatus as defined in claim 19, further comprising a second measuring device measures said punch/die set and/or said punch hole subsequent to returning said disk before said spool core mounting station, to obtain measured information;

wherein said detector device detects occurrence of deposition of said disk on said punch/die set in accordance with said measured information, and if said deposition occurs, considers said disk unacceptable due to said overlay on one subsequent disk.

21. A flexible disk inspecting apparatus as defined in claim 18, wherein said disk detected unacceptable has burr and/or deposit, and/or is defective.

22. A flexible disk inspecting apparatus as defined in claim 18, wherein said measuring device is a solid-state pick-up device for picking up said disk;

said detector device includes:

an image processor for producing measured pattern data from said image data from said pick-up device, to represent density distribution of said disk by way of said disk information;

a controller for comparing said measured pattern data with said reference information.

23. A flexible disk inspecting apparatus as defined in claim 18, further comprising an eliminator device, controlled by said controller, for eliminating said unacceptable disk before said spool core mounting station.

24. A flexible disk inspecting apparatus as defined in claim 18, further comprising an eliminator device, controlled by said controller, for eliminating said unacceptable disk and said spool core after said spool core mounting station from a path toward a succeeding assembling station.

25. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set; said disk being returned to a punch hole formed in said disk and conveyed with said sheet; said disk being removed from said punch hole by a disk remover unit before conveyance to a spool core mounting station; said flexible disk inspecting apparatus comprising:

a measuring device for measuring said punch/die set, said punch hole subsequent to returning said disk, said disk remover unit, and/or said disk subsequent to removal from said punch hole before said spool core mounting station, to obtain measured information;

a controller for evaluating said measured information, to inspect occurrence of overlay of said disk on another disk before said spool core mounting station, so as to detect said disk unacceptable if said overlay occurs; and an eliminator device, controlled by said controller, for eliminating said unacceptable disk before said spool core mounting station, or for eliminating said unacceptable disk and said spool core after said spool core mounting station from a path toward a succeeding assembling station.

26. A flexible disk inspecting apparatus as defined in claim 25, further comprising:

a second measuring device, disposed upstream from said spool core mounting station, for measuring a shape of said disk to obtain disk information;

a memory for previously storing reference information; and wherein said controller compares said disk information with said reference information read from said memory, so as to detect said disk unacceptable if said disk information is different from said reference information.

27. A flexible disk inspecting apparatus as defined in claim 25, wherein said measuring device detects occurrence of deposition of said disk on said punch/die set in accordance with said measured information, and if said deposition occurs, said controller considers said disk unacceptable due to said overlay on one subsequent disk.

28. A flexible disk inspecting apparatus as defined in claim 27, wherein said measuring device is a photoelectric switch of a reflection type, including:

a projector for applying an electromagnetic ray to a blade of said punch/die set; and a receiver for measuring said electromagnetic ray reflected by said blade by way of said measured information, for said occurrence detection of said disk deposition.

29. A flexible disk inspecting apparatus as defined in claim 25, wherein said measuring device checks existence of said disk in said punch hole; and if said disk does not exist, said controller detects said disk deposited on said punch/die set, and considers said disk unacceptable due to said overlay on one subsequent disk cuttable by said punch/die set.

30. A flexible disk inspecting apparatus as defined in claim 29, wherein said measuring device is a photoelectric switch of a transmission or reflection type, including:

a projector for applying an electromagnetic ray to said sheet in a station downstream from said punch/die set relative to conveyance of said sheet;

a receiver for measuring said electromagnetic ray from said sheet by way of said measured information.

31. A flexible disk inspecting apparatus as defined in claim 29, wherein said disk remover unit includes a sucker, disposed over said sheet, for sucking said disk from said punch hole in air suction; and said measuring device is a pressure switch for measuring sucking pressure of said sucker during said air suction by way of said measured information, and if said sucking pressure is zero, said controller detects said disk not existing in said punch hole.

32. A flexible disk inspecting apparatus as defined in claim 25, wherein said disk is translucent;

said measuring device is a photoelectric switch of a transmission type, including: a projector for applying an electromagnetic ray to said disk conveyed serially after removal from said punch hole; and a receiver for detecting said electromagnetic ray transmitted through said disk by way of said measured information;

said controller compares transmitted intensity of said electromagnetic ray with a predetermined threshold value, and if said transmitted intensity is lower than said threshold value, detects said disk unacceptable due to said overlay.

33. A flexible disk inspecting apparatus as defined in 32, wherein said disk includes an axial hole formed in a center for receiving insertion of said spool core;

said projector directs said electromagnetic ray to a peripheral portion of said disk defined about said axial hole.

34. A flexible disk inspecting apparatus as defined in claim 25, wherein said measuring device measures thickness of said disk by way of said measured information;

said controller compares said thickness with a predetermined limit value, and if said thickness is greater than said limit value, said disk being detected unacceptable due to said overlay.

35. A flexible disk inspecting apparatus as defined in claim 34, wherein said measuring device includes:

a base plate contacted on a first face of said disk conveyed serially after removal from said punch hole; and an optical rangefinder, disposed opposite to said base plate with reference to said disk, for optically measuring a distance to a second face of said disk reverse to said first face;

said controller obtains thickness of said disk from positions of said base plate and said rangefinder, and said distance measured.

36. A flexible disk inspecting apparatus as defined in claim 34, wherein said measuring device is a three-dimensional measuring machine, including:

a base plate contacted on a first face of said disk conveyed serially after removal from said punch hole;

a probe contacted on a second face of said disk reverse to said first face;

said controller detects positions of said base plate and said probe, and obtains thickness of said disk from said positions of said base plate and said probe.

37. A flexible disk inspecting apparatus as defined in claim 25, wherein said measuring device measures weight of said disk by way of said measured information;

said controller compares said weight with a predetermined limit value, and if said weight is greater than said limit value, said disk being detected unacceptable due to said overlay.

38. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set before conveyance to a spool core mounting station; said flexible disk inspecting apparatus comprising:

a movable conveyor plate disposed over said disk conveyed serially toward said spool core mounting station;

a disk sucker for sucking said disk of said conveyor plate at a sucking force short of two times as much as weight of said disk, said conveyor plate being moved during sucking operation, to allow dropping said disk unacceptably overlaid on another disk without further conveyance.

39. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set before conveyance to a spool core mounting station; said flexible disk inspecting apparatus comprising:

a solid-state pick-up device, disposed upstream from said spool core mounting station, for picking up said disk;

an image processor for producing measured pattern data from image data from said pick-up device, to represent density distribution of said disk;

a memory for previously storing reference pattern data; and a controller for comparing said measured pattern data with said reference pattern data, so as to detect said disk unacceptable if said measured pattern data is different from said reference pattern data.

40. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set before conveyance to a spool core mounting station; said flexible disk inspecting apparatus comprising:

a photoelectric switch of a reflection type, including: a projector for applying an electromagnetic ray to a blade of said punch/die set after cutting out said disk; and a receiver for measuring said electromagnetic ray reflected by said blade; and a controller for evaluating said measured electromagnetic ray, to inspect occurrence of deposition of said disk on said punch/die set, and if said deposition occurs, said controller considering said disk likely to overlie on one subsequent disk.

41. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set; said disk being returned to a punch hole formed in said disk and conveyed with said sheet; said disk being removed from said punch hole by a disk remover unit before conveyance to a spool core mounting station; said flexible disk inspecting apparatus comprising:

a photoelectric switch of a transmission or reflection type, including: a projector for applying an electromagnetic ray to said sheet in a station downstream from said punch/die set relative to conveyance of said sheet; a receiver for measuring said electromagnetic ray from said sheet; and a controller for evaluating said measured electromagnetic ray, to check existence of said disk in said punch hole, and if said disk does not exist, said controller considering said disk likely to overlie on one subsequent disk cuttable by said punch/die set.

42. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set; said disk being returned to a punch hole formed in said disk and conveyed with said sheet; said disk being removed from said punch hole by a sucker in air suction before conveyance to a spool core mounting station; said flexible disk inspecting apparatus comprising:

a pressure switch for measuring sucking pressure of said sucker during said air suction; and a controller for evaluating said measured sucking pressure, and if said sucking pressure is zero, said controller detecting said disk not existing in said punch hole, and considering said disk likely to overlie on one subsequent disk cuttable by said punch/die set.

43. An apparatus for inspecting a flexible disk used in a photo film cassette, said photo film cassette having a spool core about which said photo film is wound in a roll form; a cassette shell for containing said spool core in rotatable fashion; said disk being secured to each of two ends of said spool core, for regulating each of edges of said photo film; material of said disk being thermoplastic synthetic resin sheet; said sheet being subjected to vacuum forming, air-pressure forming, or vacuum/air-pressure forming in combination of said vacuum forming and said air-pressure forming, to form a disk-like portion; said disk being cut out of said disk-like portion by a punch/die set before conveyance to a spool core mounting station; said flexible disk inspecting apparatus comprising:

said disk being translucent;

a photoelectric switch of a transmission type, including: a projector for applying an electromagnetic ray to said disk conveyed serially; and a receiver for detecting said electromagnetic ray transmitted through said disk; and a controller for comparing transmitted intensity of said electromagnetic ray with a predetermined threshold value, and if said transmitted intensity is lower than said threshold value, said controller detecting said disk overlaid on another disk.

* * * * *